US012600931B2

(12) United States Patent
Coppeta et al.

(10) Patent No.: US 12,600,931 B2
(45) Date of Patent: Apr. 14, 2026

(54) MICROFLUIDIC CELL CULTURE PLATE FOR AIR-LIQUID INTERFACE AND 3D CULTURED TISSUE APPLICATIONS

(71) Applicant: The Charles Stark Draper Laboratory Inc., Cambridge, MA (US)

(72) Inventors: Jonathan R. Coppeta, Windham, NH (US); Hesham Azizgolshani, Belmont, MA (US); Brian P. Cain, Cambridge, MA (US); Brett C. Isenberg, Newton, MA (US); Joseph L. Charest, Jamaica Plain, MA (US); Else M. Vedula, Stoneham, MA (US); Ashley L. Gard, Dorchester, MA (US); Ryan S. Maloney, Cambridge, MA (US); Jeffrey T. Borenstein, West Roxbury, MA (US); Rebeccah J. Luu, Cambridge, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 347 days.

(21) Appl. No.: 17/246,028

(22) Filed: Apr. 30, 2021

(65) Prior Publication Data

US 2021/0340477 A1    Nov. 4, 2021

Related U.S. Application Data

(60) Provisional application No. 63/018,791, filed on May 1, 2020.

(51) Int. Cl.
| | |
|---|---|
| *C12M 3/06* | (2006.01) |
| *C12M 1/00* | (2006.01) |
| *C12M 1/12* | (2006.01) |
| *C12M 1/32* | (2006.01) |
| *C12M 1/42* | (2006.01) |

(52) U.S. Cl.
CPC ............ *C12M 23/16* (2013.01); *C12M 23/12* (2013.01); *C12M 23/22* (2013.01); *C12M 25/04* (2013.01); *C12M 29/00* (2013.01)

(58) Field of Classification Search
CPC ...... C12M 23/16; C12M 23/12; C12M 23/22; C12M 25/04; C12M 25/06; C12M 25/08; C12M 29/00; B01L 2300/0858
See application file for complete search history.

(56) References Cited

U.S. PATENT DOCUMENTS

| | | | |
|---|---|---|---|
| 2004/0069717 A1 | 4/2004 | Laurell et al. | |
| 2013/0171682 A1 | 7/2013 | Hung et al. | |

(Continued)

FOREIGN PATENT DOCUMENTS

| | | | | | |
|---|---|---|---|---|---|
| EP | 3088076 A1 | * | 11/2016 | ........ | B01L 3/502707 |
| WO | WO-2013086329 A1 | * | 6/2013 | ........ | B01L 3/502715 |

(Continued)

OTHER PUBLICATIONS

Extended European Search Report on EP Appl. Ser. No. 21171718.6 dated Oct. 7, 2021 (6 pages).

(Continued)

*Primary Examiner* — Elizabeth A Robinson
*Assistant Examiner* — Brittany I Fisher
(74) *Attorney, Agent, or Firm* — Brooks Kushman, P.C.

(57) ABSTRACT

The present disclosure describes systems and methods for providing culturing of a number of various tissue types in an air-liquid configuration in a high-throughput format and allowing co-culture of cells as well as application of physiologically relevant flow. A microfluidic cell culturing device is provided that includes a first channel having a first inlet port and a second inlet port, the first channel defined in a first layer. The microfluidic cell culturing device includes a membrane layer having a first surface coupled to the first (Continued)

layer defining the first channel, the membrane layer comprising semipermeable membrane that forms at least a portion of a surface of the first channel. The microfluidic cell culturing device includes a chamber defined in a second layer that exposes a portion the membrane layer to an external environment, wherein the chamber overlaps a portion of the first channel across the membrane layer.

20 Claims, 34 Drawing Sheets

(56) References Cited

U.S. PATENT DOCUMENTS

| | | | | |
|---|---|---|---|---|
| 2015/0352546 A1 * | 12/2015 | Egeler | ...................... | B05D 1/18 |
| | | | | 422/549 |
| 2018/0120294 A1 * | 5/2018 | Collins | .................. | C12M 35/02 |
| 2018/0171276 A1 * | 6/2018 | Kilic | ...................... | C12M 25/02 |
| 2021/0062129 A1 * | 3/2021 | Nawroth | ............ | G01N 33/5044 |

FOREIGN PATENT DOCUMENTS

| | | | | | |
|---|---|---|---|---|---|
| WO | WO-2015032889 A1 * | 3/2015 | ............ | C12M 21/08 |
| WO | WO-2016069892 A1 * | 5/2016 | ............ | C12M 1/268 |
| WO | WO-2017/096297 A1 | 6/2017 | | |
| WO | WO-2017/175236 A1 | 10/2017 | | |

OTHER PUBLICATIONS

EP Office Action on EP Appl. Ser. No. 21171718.6 dated Mar. 12, 2024 (4 pages).

* cited by examiner

200A

200B

300A

300B

400B

*Example plate map*

500B
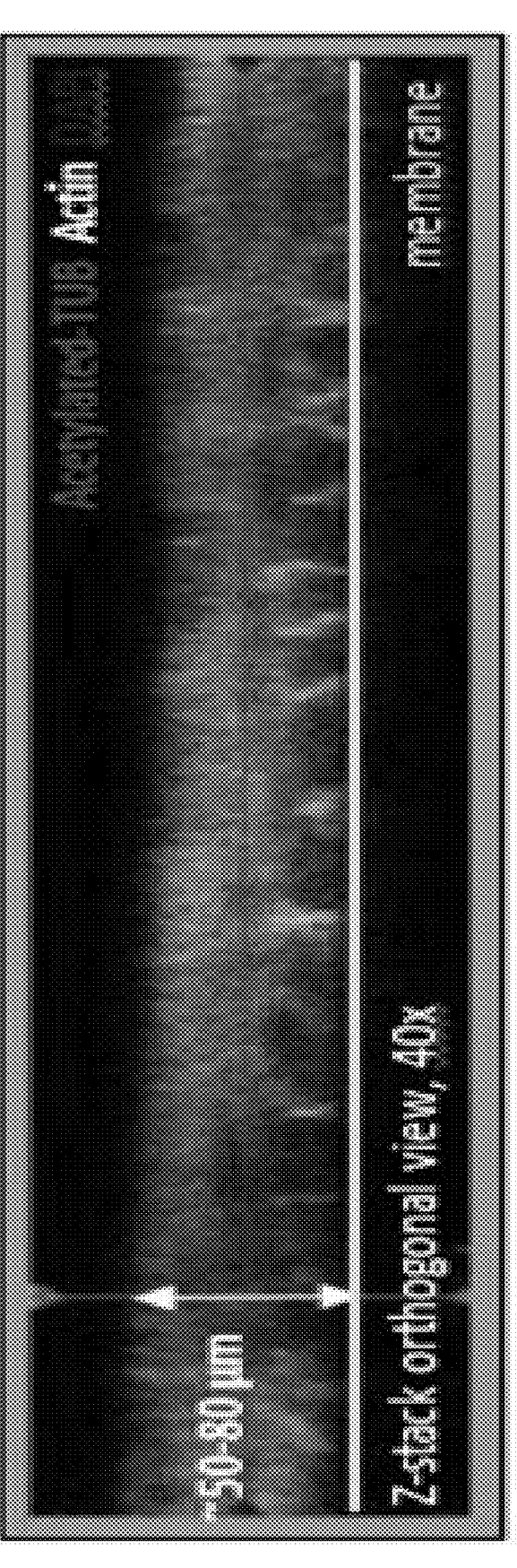
FIG. 5B

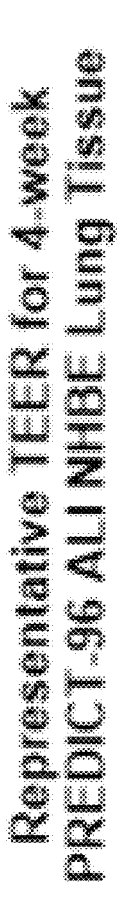
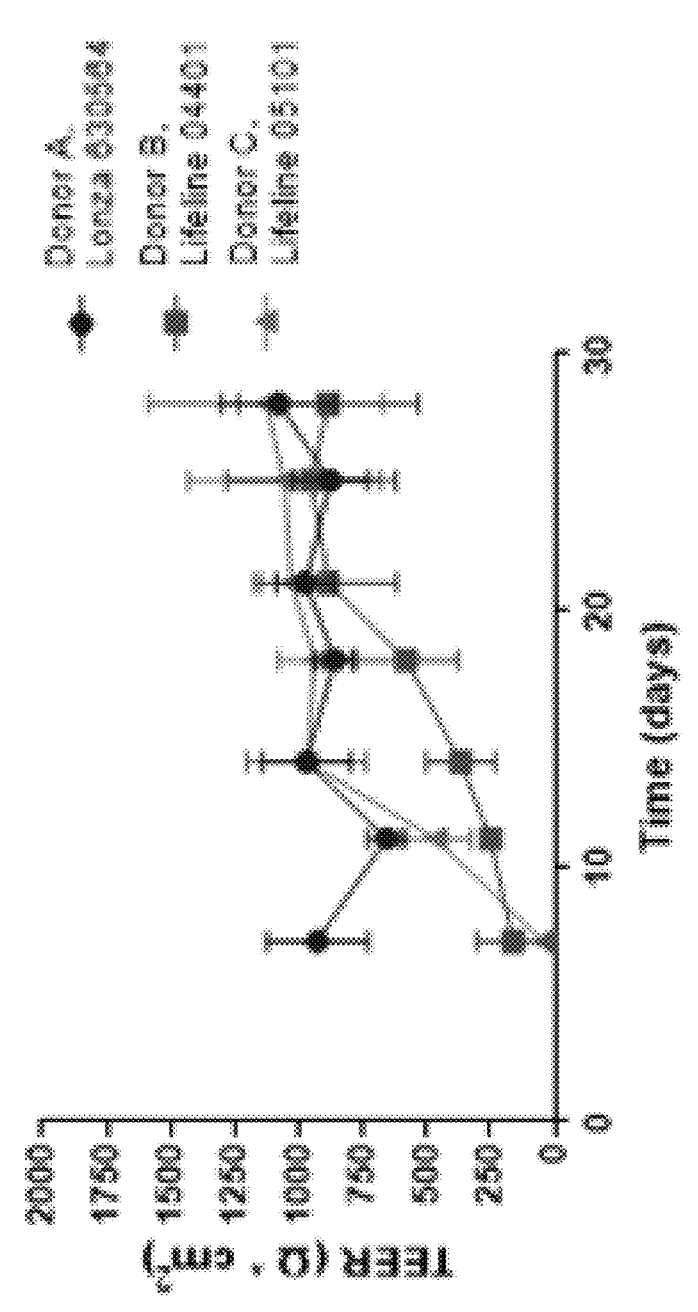
500C
Representative TEER for 4-week PREDICT-96 ALI NHBE Lung Tissue
FIG. 5C

1200B

1200A

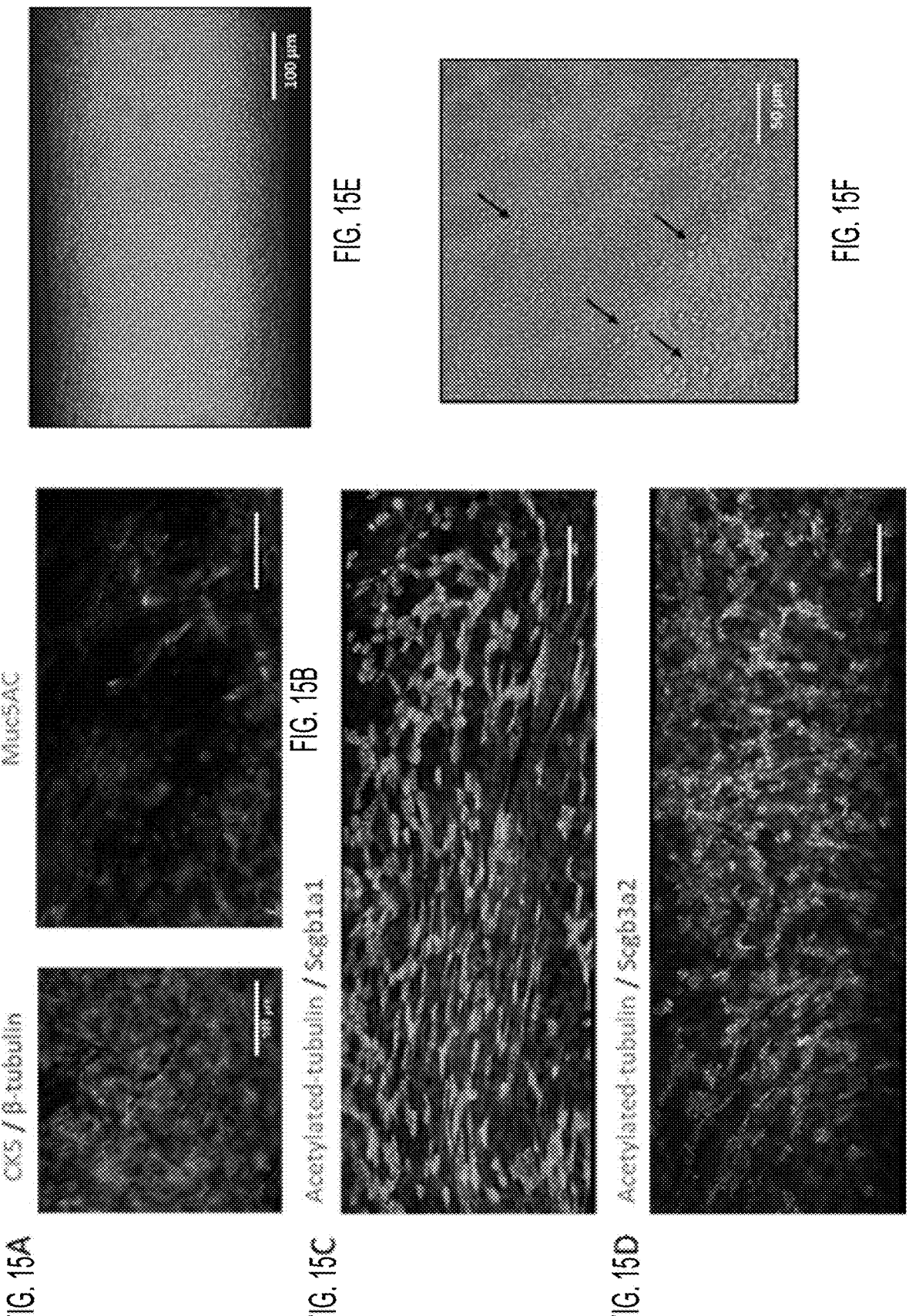

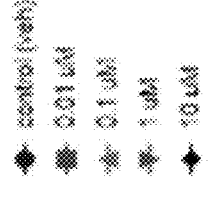
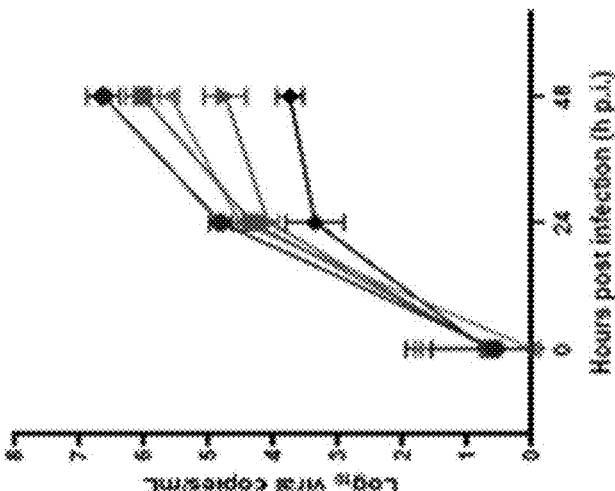
FIG. 18B
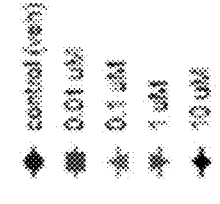
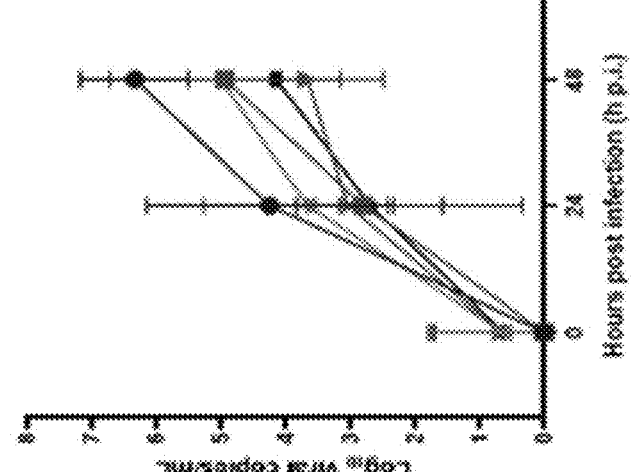
FIG. 18A

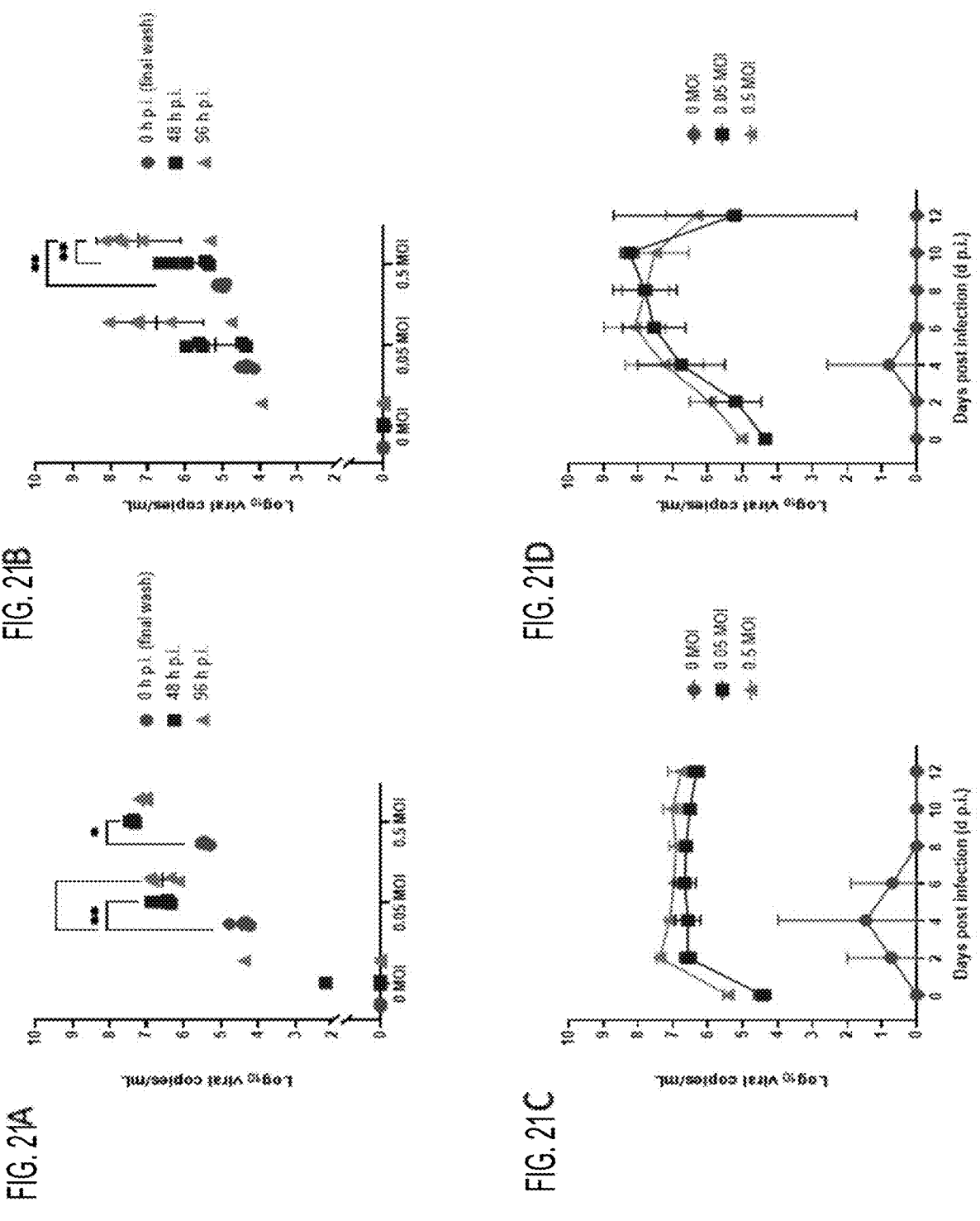

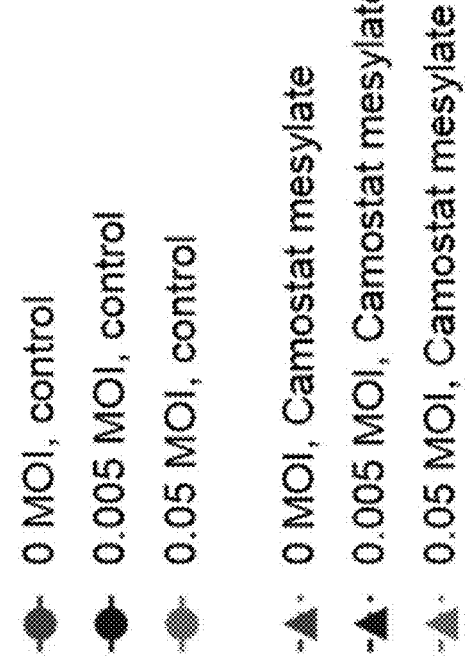
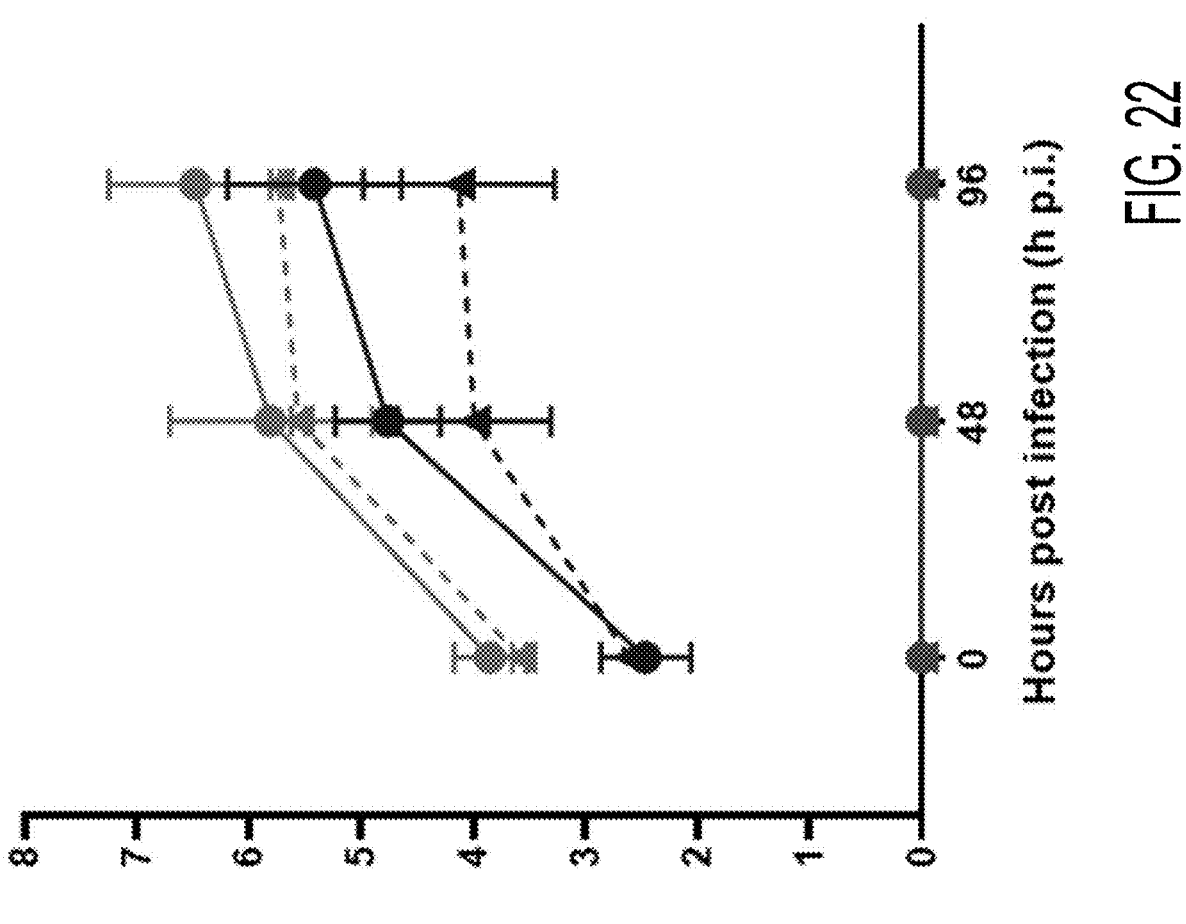
FIG. 22

MICROFLUIDIC CELL CULTURE PLATE FOR AIR-LIQUID INTERFACE AND 3D CULTURED TISSUE APPLICATIONS

CROSS-REFERENCE TO RELATED PATENT APPLICATIONS

This application claims the benefit of and priority to U.S. Provisional Patent Application No. 63/018,791, filed May 1, 2020, entitled "MICROFLUIDIC CELL CULTURE PLATE FOR AIR-LIQUID INTERFACE AND 3-D CULTURED TISSUE APPLICATIONS," the content of which is incorporated herein by reference in its entirety.

BACKGROUND OF THE DISCLOSURE

Microfluidic devices can include features such as channels, chambers, and wells. Such devices can be used for culturing cells, which may be observed under controlled conditions, for example to test efficacy of therapeutic substances. Conventional microfluidic devices can be difficult to efficiently use for different types of cells as well as co-culturing of cells.

SUMMARY OF THE DISCLOSURE

The present disclosure describes systems and methods for providing culturing of a number of various tissue types in an air-liquid interface (ALI) configuration in a high-throughput format and allowing co-culture of cells as well as application of physiologically relevant flow. The solution of the present disclosure also allows for measurement of tissue barrier function through transepithelial electrical resistance (TEER) measurements. The solution of the present disclosure also accommodates the culture of 3D printed and multilayer culture of tissues, adherent cells, or cells suspended in a solution.

There is evidence that certain cultured cells perform better on membranes with smaller pore sizes. This creates a challenge in seeding of the cells onto the membrane, in particular in the overlap region of the microfluidic channels of the standard and pressure seal type of devices. This challenge is alleviated through the systems and method of the present solution.

At least one aspect of the present disclosure is directed to a microfluidic cell culturing device. The microfluidic cell culturing device can include a first channel having a first inlet port and a second inlet port. The first channel can be defined in a first layer. The microfluidic cell culturing device can include a membrane layer having a first surface coupled to the first layer defining the first channel. The membrane layer comprising a semipermeable membrane that forms at least a portion of a surface of the first channel. The microfluidic cell culturing device can include a chamber defined in a second layer coupled to a second surface of the membrane layer. The chamber can expose a portion of the second surface of the membrane layer to an external environment. The chamber can overlap a portion of the first channel across the membrane layer.

In some implementations, the microfluidic cell culturing device can include one or more conductive traces configured to attach to an electrical measurement device. In some implementations, at least one of the first inlet port the second inlet port, or the chamber is coupled to a reservoir of a culture plate. In some implementations, the chamber is configured to receive suspension cells or adherent cells, and the exposed portion of the second surface of the membrane layer is configured to culture one or more cells. In some implementations, the first layer is coupled to the membrane layer using thermal compression.

In some implementations, the chamber further comprises a step feature configured to retain cell suspension during seeding of the microfluidic cell culturing device. In some implementations, the step feature has a height in a range of 250 microns to 2.5 millimeters. In some implementations, the step feature further comprises a draft angle configured to reduce bulging of a cell suspension droplet positioned in the chamber. In some implementations, the chamber comprises a rectangular footprint or a slotted footprint. In some implementations, the microfluidic cell culturing device can include an optically clear layer coupled to the first layer. In some implementations, the semipermeable membrane comprises pores can have a pore size in a range of 0.4 to 8 microns. In some implementations, the first layer or the second layer can include one or more of cyclo-olefin polymers, polyetherimide, polystyrene, polycarbonate, or polymethylmethacrylate.

At least one other aspect of the present disclosure is directed to a culture plate. The culture plate can include a plurality of well reservoirs. The culture plate can include a plurality of microfluidic devices. Each of the plurality of microfluidic devices can include a first channel having a first inlet port and a second inlet port. The first channel can be defined in a first layer. Each of the plurality of microfluidic devices can include a membrane layer having a first surface coupled to the first layer defining the first channel. The membrane layer can include a semipermeable membrane that forms at least a portion of a surface of the first channel. Each of the plurality of microfluidic devices can include a chamber defined in a second layer coupled to a second surface of the membrane layer. The chamber can expose a portion of the second surface of the membrane layer to an external environment. The chamber can overlap a portion of the first channel across the membrane layer.

In some implementations, the chamber of each of the plurality of microfluidic devices further comprises one or more conductive traces configured to attach to an electrical measurement device. In some implementations, at least one of the first inlet port, the second inlet port, or the chamber, of each of the plurality of microfluidic devices, is coupled to a respective well reservoir of the plurality of well reservoirs. In some implementations, the chamber of each of the plurality of microfluidic devices is configured to receive suspension cells or adherent cells, and the exposed portion of the second surface of the membrane layer of each of the plurality of microfluidic devices is configured to culture one or more cells.

In some implementations, the chamber of each of the plurality of microfluidic devices further comprises a step feature configured to retain cell suspension during seeding of the plurality of microfluidic devices. In some implementations, the step feature has a height in a range of 250 microns to 2.5 millimeters. In some implementations, the step feature further comprises a draft angle configured to reduce bulging of a cell suspension droplet positioned in the chamber. In some implementations, the first layer or the second layer of each of the plurality of microfluidic devices comprises one or more of cyclo-olefin polymers, polyetherimide, polystyrene, polycarbonate, or polymethylmethacrylate. In some implementations, the culture plate can include one or more pumps each in fluid communication with a respective first inlet port or a respective second inlet port of a respective microfluidic device of the plurality of microfluidic devices.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification. Aspects can be combined and it will be readily appreciated that features described in the context of one aspect of the invention can be combined with other aspects. Aspects can be implemented in any convenient form.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

FIG. 4B depicts a plate map of the well plate illustrated in FIGS. 1A and 1B for three donor populations, in accordance with one or more implementations;

FIG. 5B depicts a cross-section of the pseudo-stratified epithelial layer, in accordance with one or more implementations;

FIG. 5C depicts TEER measurements for three different donor populations of normal human bronchial epithelial cells, in accordance with one or more implementations;

FIGS. 15A, 15B, 15C, 15D, 15E, and 15F depict panels illustrating establishment of mature tissue with pseudostratified morphology, approximately 30-50 μm thick from freshly harvested airway epithelial cells obtained from living research bronchoscopy donor DH01, in accordance with one or more implementations;

FIGS. 18A and 18B depict RT-qPCR analyses for viral copies of the apical wash of ALI airway tissue at 24 and 48 h p.i. in absence (blue) or presence (red=0.01 μM, green=0.1 μM, violet=1 μM, black=10 μM) of oseltamivir (Tamiflu) for two donors, in accordance with one or more implementations;

FIGS. 21A, 21B, 21C, and 21D depict graphs relating to the infection of coronavirus strains in ALI models; and FIG. 22 depicts a graph relating to the efficacy of camostat mesylate against hCOV-NL63-inoculated ALI airway tissue.

DETAILED DESCRIPTION

Figure 1A:
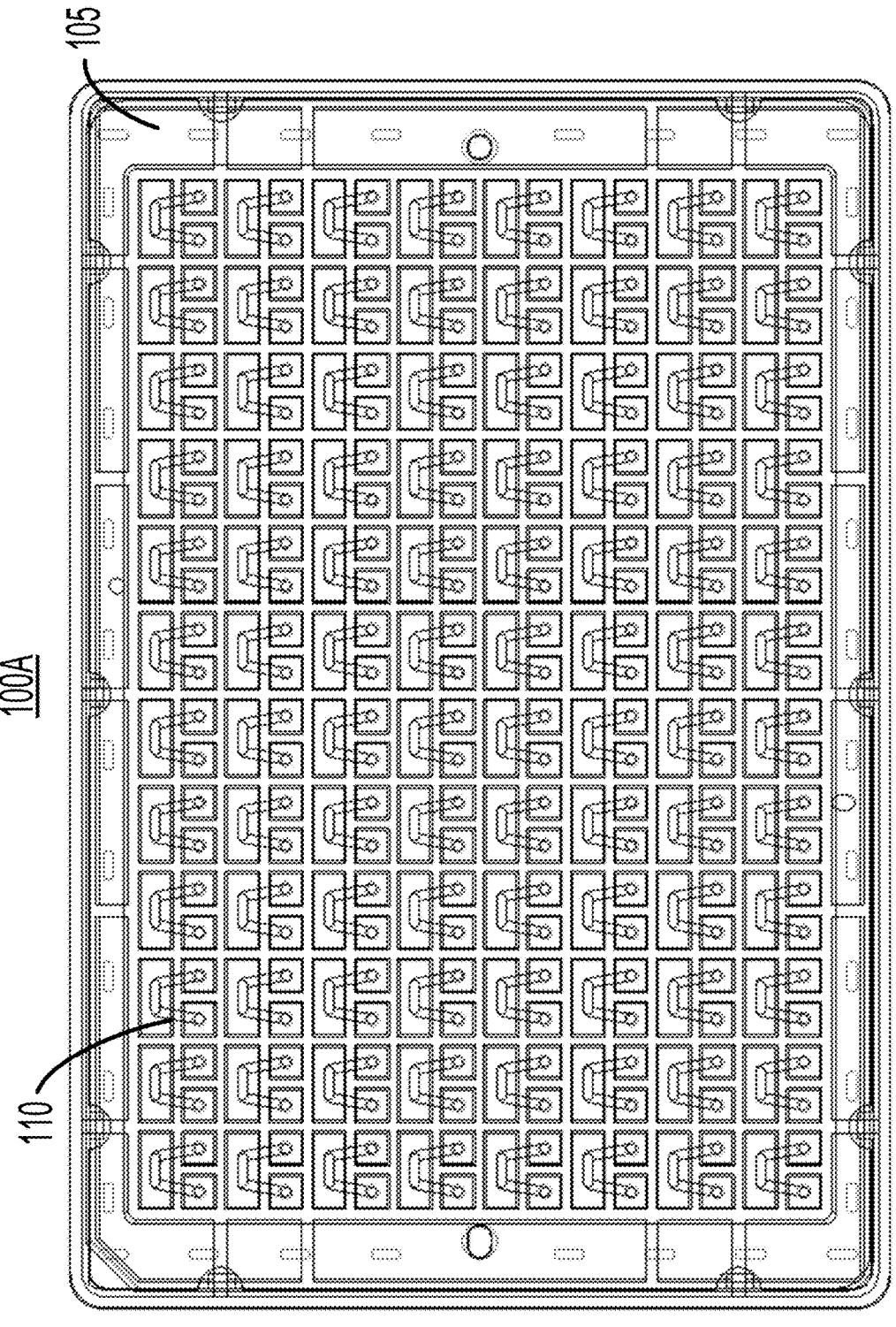
FIGS. 1A and 1B illustrate top views of an embodiment of a well plate including a number of example microfluidic devices, in accordance with one or more implementations.

The various concepts introduced above and discussed in greater detail below may be implemented in any of numerous ways, as the described concepts are not limited to any particular manner of implementation. Examples of specific implementations and applications are provided primarily for illustrative purposes.

Influenza and other respiratory viruses represent a tremendous threat to human health and to the economy of the United States and across the world, and are a major cause of pandemics such as the current COVID-19 crisis. One of the greatest barriers to the development of effective therapeutic agents to treat influenza, coronaviruses and other infections of the respiratory tract is the absence of a robust preclinical model for many of these diseases. Preclinical studies currently rely on a combination of high-throughput, low-fidelity in vitro screening with cell lines such as A549, Calu-2 or Vero-E6 cells, and low-throughput animal models that provide a poor correlation to human clinical responses. The systems and methods described herein provide a high-throughput, human primary airway epithelial cell-based platform device, that can model influenza and coronavirus infections. In addition, the systems and methods described herein can be used in connection with measurement devices to provide multiple readouts capable of evaluating the efficacy of therapeutic agents in an in vitro system. This capability fills a critical gap in the rapid assessment of the therapeutic efficacy of various small molecules and antiviral agents against pandemic strains of influenza and SARS-CoV-2.

A pandemic respiratory virus, such as influenza or the current outbreak of coronavirus, represents one of the greatest threats to human health and mankind. For influenza, the development of efficacious and lasting vaccinations has been challenged by the occurrence of both antigenic drift and shift, causing the effectiveness of vaccines to vary widely for seasonal flu strains. Currently, four antivirals are in wide use for treatment of influenza, three neuraminidase inhibitors and the recent addition of baloxivir; these treatments are generally efficacious, but genetic changes to the circulating viruses present challenges similar to those encountered during the development of vaccines. The current pandemic of the novel coronavirus COVID-19 has spurred accelerated development of a vaccine, but the timeline is not rapid enough to blunt the morbidity and mortality associated with the current wave of infection. Therefore, a critical element of medical treatment strategy is the application of antiviral medications identified from FDA-approved drugs originally targeting other infections.

However, the process for identifying and evaluating antiviral therapeutics for efficacy against newly identified viral strains is challenging. For influenza A viruses (IAV), standard approaches begin with the inoculation of cell lines in conventional culture well plates, commonly using MDCK or Calu-3 cells. While these cells infect easily and provide a rapid early assessment of the potential efficacy of a therapeutic to IAV, they lack the relevant mechanisms and pathways of human airway or lower lung infection and are therefore often not accurate predictors of human clinical efficacy. For coronaviruses, Calu-3 or Vero E6 cells are often used for similar reasons, but again differ in key aspects from airway and alveolar epithelium. Animal models of IAV include rodent models such as mice, rats, and guinea pigs, but also ferrets and macaques as potentially more species-relevant platforms for evaluation. These models often fail to recapitulate key aspects of human infection and therefore provide a poor correlation as a basis for guiding clinical trial strategy. Similar challenges are presented for COVID-19, where the low-throughput and low availability of these animal models, combined with concerns about their predictive power, are forcing early and often high-risk testing in humans.

These challenges with preclinical models have spurred the development of cell culture platforms comprising human primary cells in a microfluidic environment, sometimes referred to herein as microphysiological systems (MPS) or organs-on-chips. For airway or alveolar models, human primary cells are cultured at an air-liquid interface (ALI), representing a suitable analogue for the respiratory barrier tissues that mimics mucus formation, mucociliary flow and a range of physiologically relevant responses. However, in practice, the integration of human primary cells or stem cell-derived populations in a physiologically-relevant microenvironment has been severely gated by several factors.

These include low-throughput, system complexity, a lack of relevant readouts, use of research-grade materials and components, and, an absence of confidence in the in vitro-in vivo correlation (IVIVC) for these technologies. Provided herein are systems and methods for providing culturing of a number of various tissue types, including adherent cells or suspension cells, in an air-liquid interface (ALI) configuration in a high-throughput format and allowing co-culture of cells as well as application of physiologically relevant flow. The solution of the present disclosure solves the above-identified issues, and also allows for measurement of tissue barrier function through transepithelial electrical resistance (TEER) measurements. The solution of the present disclosure also accommodates the culture of 3D printed and multilayer culture of tissues. In addition, provided are experimental results of the system applied toward IAV and coronavirus infection, through an ALI configuration that enables simultaneous evaluation of experiments across various viral strains, multiplicities of infection, human donors, time points and statistically significant replicates, all on a single 96-well instrumented plate. These results demonstrate that the systems and methods described herein can be used to model IAV and coronavirus infection and to assess in a clinically relevant way the efficacy of candidate therapeutics.

Figure 1B:
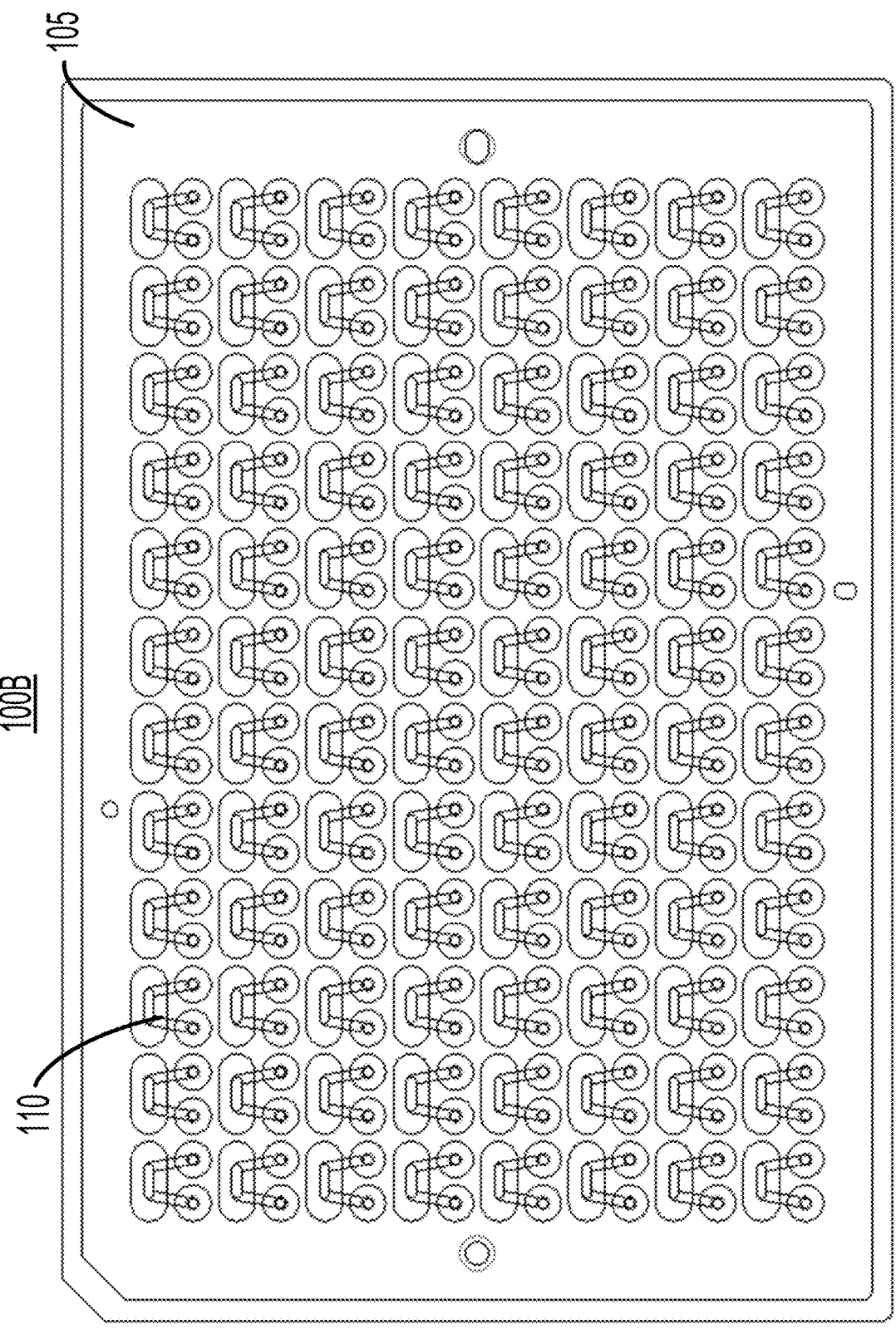

Referring now to FIGS. 1A and 1B, depicted are views 100A and 100B of a microfluidic based, bilayer tissue culture plate 105, in a high-throughput format. The culture plate 105, as shown, comprises of an array of microfluidic devices 110, which are similar to and can include all of the functionality or structure of the microfluidic devices depicted in FIGS. 2A, 2B, 3A, and 3B. In some implementations, the tissue culture plate 105 is comprised of 96 devices positioned in an 8×12 array, but many other configurations can be implemented. For example, one such arrangement can include a rectangular grid pattern. Other arrangements can include a circulator arrangement, a honeycomb arrangement, or any other type of arrangement.

The culture plate 105 can be made up of a variety or combination of thermoplastic material including, but not limited to, cyclo-olefin polymers, polyetherimide, polystyrene, polycarbonate, and polymethylmethacrylate, among others. As described in further detail herein in connection with FIGS. 2A, 2B, 3A, and 3B, each microfluidic device 110 of the tissue culture plate 105 can include a culture chamber and a microfluidic channel separated by a microporous membrane. The culture chamber can be positioned apical to a first side of the microporous membrane and the microfluidic channel is positioned basal to the second side of the microporous membrane.

Figure 2A:
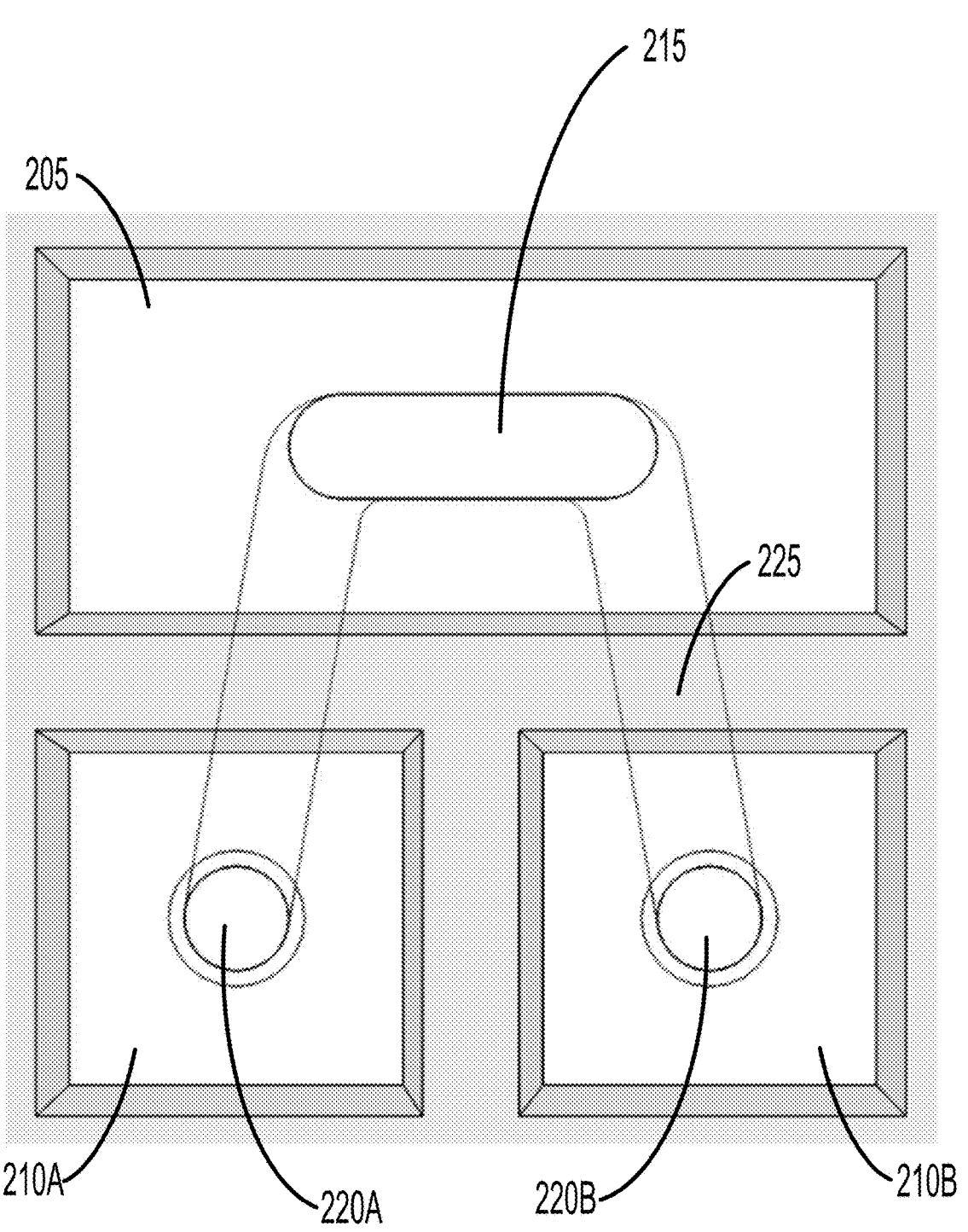
FIGS. 2A and 2B illustrate views of embodiments of a microfluidic device with multiple ports, in accordance with one or more implementations.

Referring now to FIG. 2A, depicted is a view 200A of a microfluidic device, such as the microfluidic device 110 described herein above in connection with FIGS. 1A and 1B. As shown, the microfluidic device can include multiple ports, including the culture chamber port 205, and two inlet ports 210A and 210B. In some implementations, the microfluidic device can be defined by two terminating openings 220A and 220B, each of which terminate to well reservoirs 210A and 210B in a culture plate, such as the culture plate 105 described herein above in connection with FIGS. 1A and 1B. For example, the openings 220A and 220B can be coupled to one or more of the well reservoirs 210A and 210A, or the openings 220A and 220B can be formed as a part of the well reservoirs 210A and 210A of a culture plate 105. In some implementations, the geometry of the well reservoirs 210A and 210B terminating the microfluidic channel 225 can allow for a tight fit with a pipette tip, or another type of delivery mechanism, and can facilitate delivery of cells into the bottom microfluidic channel 225. In some implementations, the microfluidic channel 225 can be defined in a layer of material, as described in further detail herein in connection with FIGS. 3A and 3B.

Figure 2B:
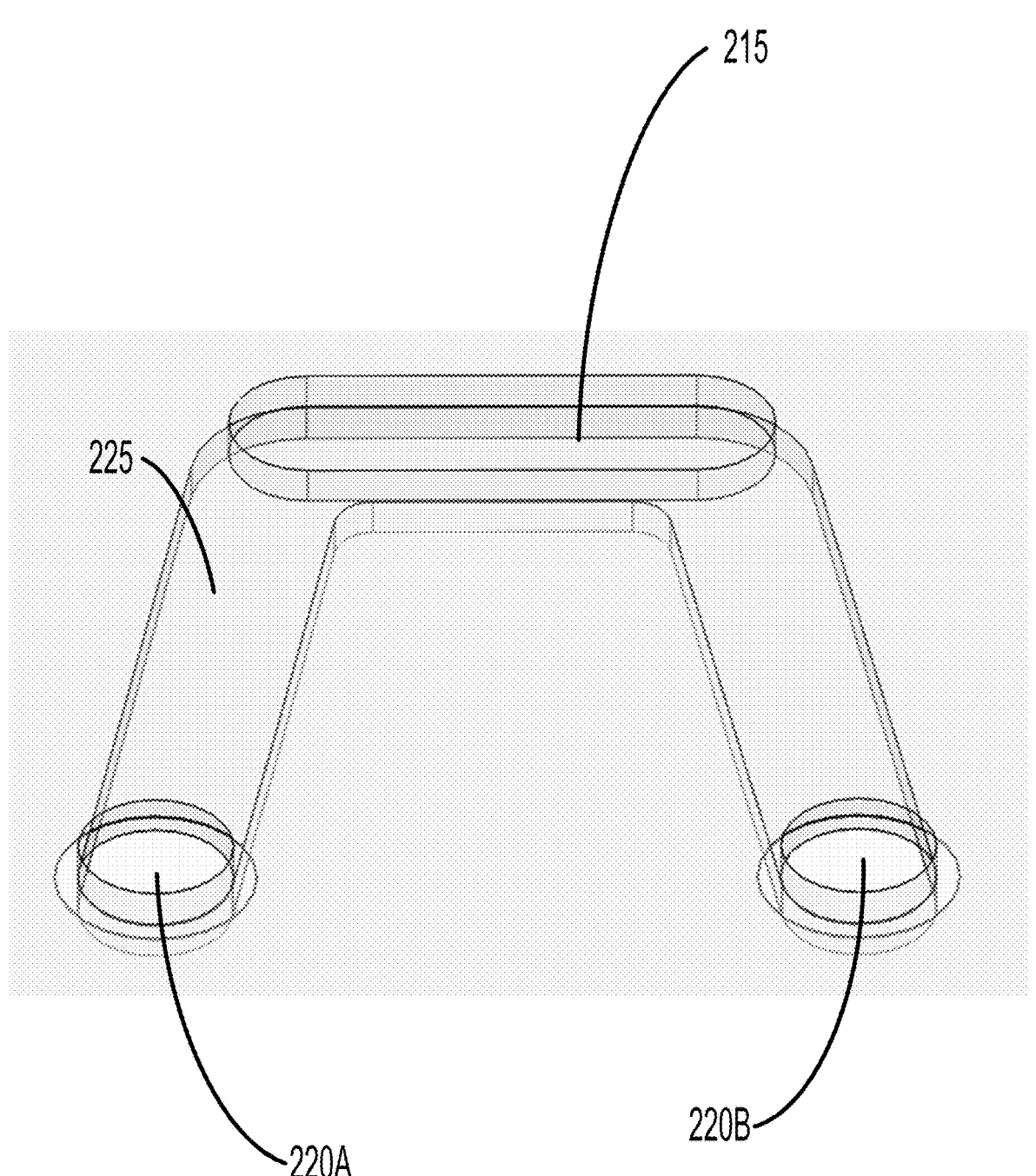

Referring now to FIG. 2B, depicted is a translucent perspective view 200B of the microfluidic channel 225 and the culture chamber 215. The microfluidic channel 225 and the apposing culture chamber 215 can have an overlap region where the two are in biochemical and physical communication across a membrane, as described in greater detail herein below in connection with FIGS. 3A and 3B. In one embodiment, the culture chamber 215 has a footprint identical to that of overlap region with the underlying microchannel. In other embodiments, the culture chamber 215 includes a larger footprint, and the overlap region is defined by a step feature (described in greater detail herein below in connection with FIGS. 10A and 10B). The step feature can serve to retain cell suspension during seeding of the microfluidic device 110 (e.g., via the openings 220A or 220B, etc.), and to limit cultured cells to the overlap region following seeding.

In some implementations, the step feature can have a height in the range of 250 microns to 2.5 millimeters, but can have other dimensions to accommodate other volumes of cell suspension. In some implementations, the step feature can include a draft angle. The draft angle can reduce bulging of a cell suspension droplet due to surface tension, and can result in a more uniform settling and seeding of the suspended cells in the overlap region. In some implementations, the culture chamber 215 can have a rectangular footprint. In some implementations, the culture chamber 215 can have a slotted format, where the culture chamber 215 is defined as one or more slots defined in the overlap region. The microfluidic channel 225 can have a uniform width between the two ports. In some implementations, the microfluidic channel 225 can have a non-uniform width, and can have a circular, or diamond shape to increase the overlap surface area. Likewise, in some implementations, the culture chamber 215 can be subdivided into 2 or more smaller chambers, which can enable seeding of multiple cell types separately or the creation of concentration gradients within the chamber.

Figure 3A:
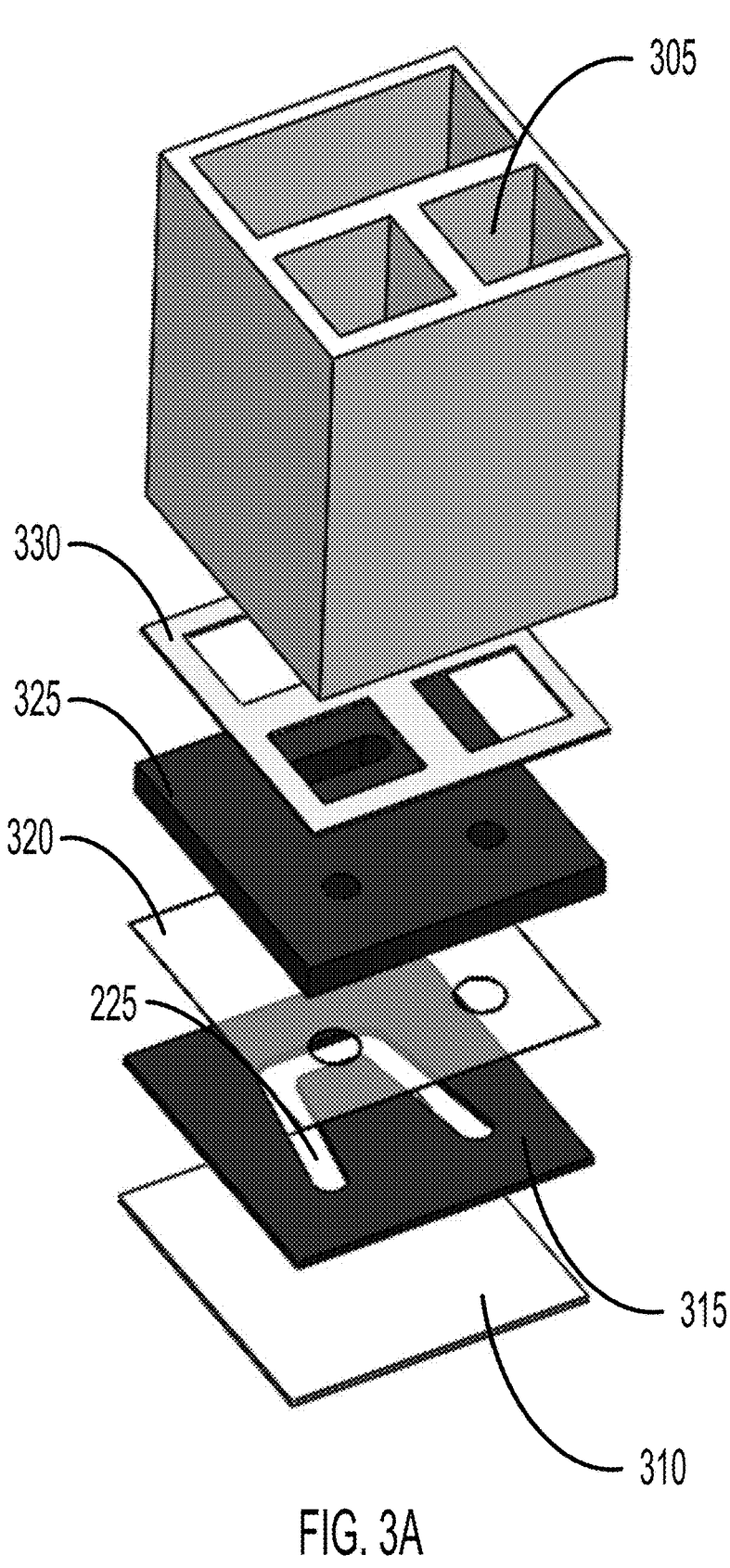
FIGS. 3A and 3B illustrate exploded and perspective views of an embodiment of a well of the well plate illustrated in FIGS. 1A and 1B, in accordance with one or more implementations.

Referring now to FIG. 3A, depicted is an exploded view of a stack of layers that make up the microfluidic device 110 described herein above in connection with FIGS. 1A, 1B, 2A, and 2B. As shown in the view 300, the microfluidic device 110 can include a base layer 310, a channel layer 315, a membrane layer 320, a chamber layer 325, a coupling layer 330, and a well reservoir 305. The base layer 310 can be formed from a variety or combination of thermoplastic material including, but not limited to, cyclo-olefin polymers, polyetherimide, polystyrene, polycarbonate, and polymethylmethacrylate, among others. In some implementations, the base layer 310 can be an optically clear layer, such as glass or a transparent plastic such as fluorinated ethylene propylene, thereby providing an optical interface to the channel 225.

A channel layer 315 can be placed on top of, and coupled to or formed as a part of, the base layer 310. As shown, the channel layer 315 can define the walls of the microfluidic channel 225, and the base layer 310 can form the bottom of the microfluidic channel 225. The channel layer 315 can be manufactured from a variety or combination of thermoplastic material including, but not limited to, cyclo-olefin polymers, polyetherimide, polystyrene, polycarbonate, and polymethylmethacrylate, among others. As shown, the microfluidic channel 225 can be formed as a recessed portion in the channel layer 315. The channel layer 315 and the microfluidic channel 225 defined therein can be may be formed by various processes, including wet etching, reactive ion etching, conventional machining, photolithography, soft lithography, injection molding, laser ablation, in situ construction, plasma etching, or any combination thereof In some implementations, the channel layer 315 can be adhered to other layers in the microfluidic devices described herein using a pressure sensitive adhesive The membrane layer 320 can include a microporous membrane. The membrane layer can be coupled to the channel layer 315, for example, by using an adhesive or other coupling technique. The microporous membrane can be made up of a variety of materials, including but not limited to polycarbonate or polyester. In some embodiments, the membrane layer 315 can be a track-etched membrane, and can have a pore size in the range of 0.4-8 microns. However, it should be understood that the membrane layer can take other forms with alternative pore sizes. In some implementations, the membrane layer 320 can be a distensible membrane, and can provide mechanical stimulation to the growing tissue through periodic stretch (e.g., using an actuator (not pictured), or other stretching device, etc.). Stretching the membrane layer 320 can be achieved, for example, using pressure, a differential applied across the culture chamber and the microfluidic channel 225, or through other techniques, such as a ring at the perimeter of the overlap region that can tension the membrane through mechanical movement. The membrane layer can form the roof of the microfluidic channel 225. In addition, as shown, the membrane layer 315 can include one or openings that define, in part, the openings 210A and 210B (reference numbers omitted in FIG. 3A for visual clarity) shown in FIGS. 2A and 2B The chamber layer 325 can be placed on top of, and coupled to, the membrane layer 320. As shown, the chamber layer 325 can define the culture chamber 215 (reference number omitted for visual clarity). Together with the channel layer 315, the chamber layer 325 can define the overlap region across the culture chamber 215. In some implementations, one or more of the chamber layer 325 or the channel layer 315 can form by a step feature (not pictured). The step feature can serve to retain cell suspension during seeding of the microfluidic device 110, and to limit cultured cells to the overlap region following seeding. The step feature is described in further detail above in connection with FIGS. 2A and 2B. As shown, the culture chamber can be open to the air above the chamber layer 315, even when subsequent layers (e.g., the coupling layer 330 or the well reservoirs 305) are coupled to the chamber layer 315. This can create an air-liquid-interface (ALI) environment for cells cultured using the microfluidic device. The chamber layer 325 can include one or more openings that align with the openings on the membrane layer 320, thereby defining, in part, the openings 210A and 210B shown in FIGS. 2A and 2B. The chamber layer 325 can be formed from a variety of materials including, but not limited to, cyclo-olefin polymers, polyetherimide, polystyrene, polycarbonate, and polymethylmethacrylate, among others. Additional implementations for the chamber layer, including step, divot, and dual divot features, are described in further detail below in connection with FIGS. 10A, 10B, 11A, 11B, 12A, and 12B.

Figures 10A, 10B:
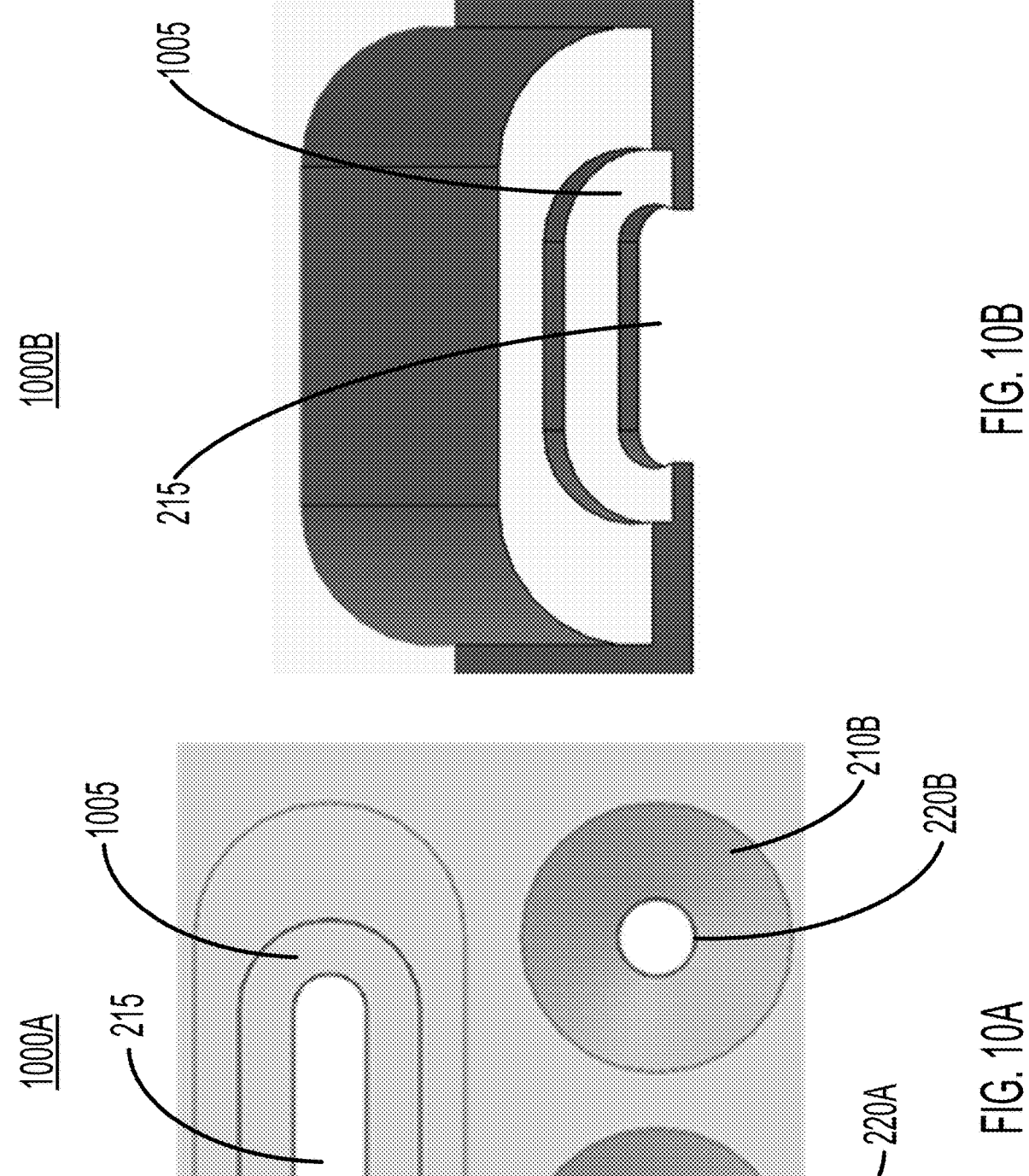
FIGS. 10A and 10B illustrate views of implementations of the microfluidic device shown in FIGS. 2A, 2B, and 2C, with an integrated step feature, in accordance with one or more implementations.

Referring now to FIGS. 10A and 10B, illustrated is a top view 1000A and a cross-sectional view 1000B of an example implementation the microfluidic device 110 described herein with an integrated step feature 1005. As shown, the microfluidic device 110 can include multiple ports, including the culture chamber 215, and two inlet ports 210A and 210B, as described in greater detail herein above in connection with FIGS. 2A and 2B. As described above, the openings 220A and 220B can be coupled to one or more of the well reservoirs 210A and 210A, or the openings 220A and 220B can be formed as a part of the well reservoirs 210A and 210A of a culture plate 105. In addition, the culture chamber 215 can include the step feature 1005. The step feature 1005 can be defined in the chamber layer 325. The step feature 1005 can serve to retain cell suspension during seeding of the microfluidic device 110 (e.g., via the openings 220A or 220B, etc.), and to limit cultured cells to the overlap region following seeding. In some implementations, the step feature 1005 can have a height in the range of 250 microns to 2.5 millimeters, but can have other dimensions to accommodate other volumes of cell suspension. In some implementations, the step feature 1005 can include a draft angle. The draft angle can reduce bulging of a cell suspension droplet due to surface tension, and can result in a more uniform settling and seeding of the suspended cells in the overlap region. In some implementations, the step feature 1005 can be used to add or remove liquid (including media and cell suspensions) to the culture chamber without disrupting the tissue directly.

Figures 11A, 11B:
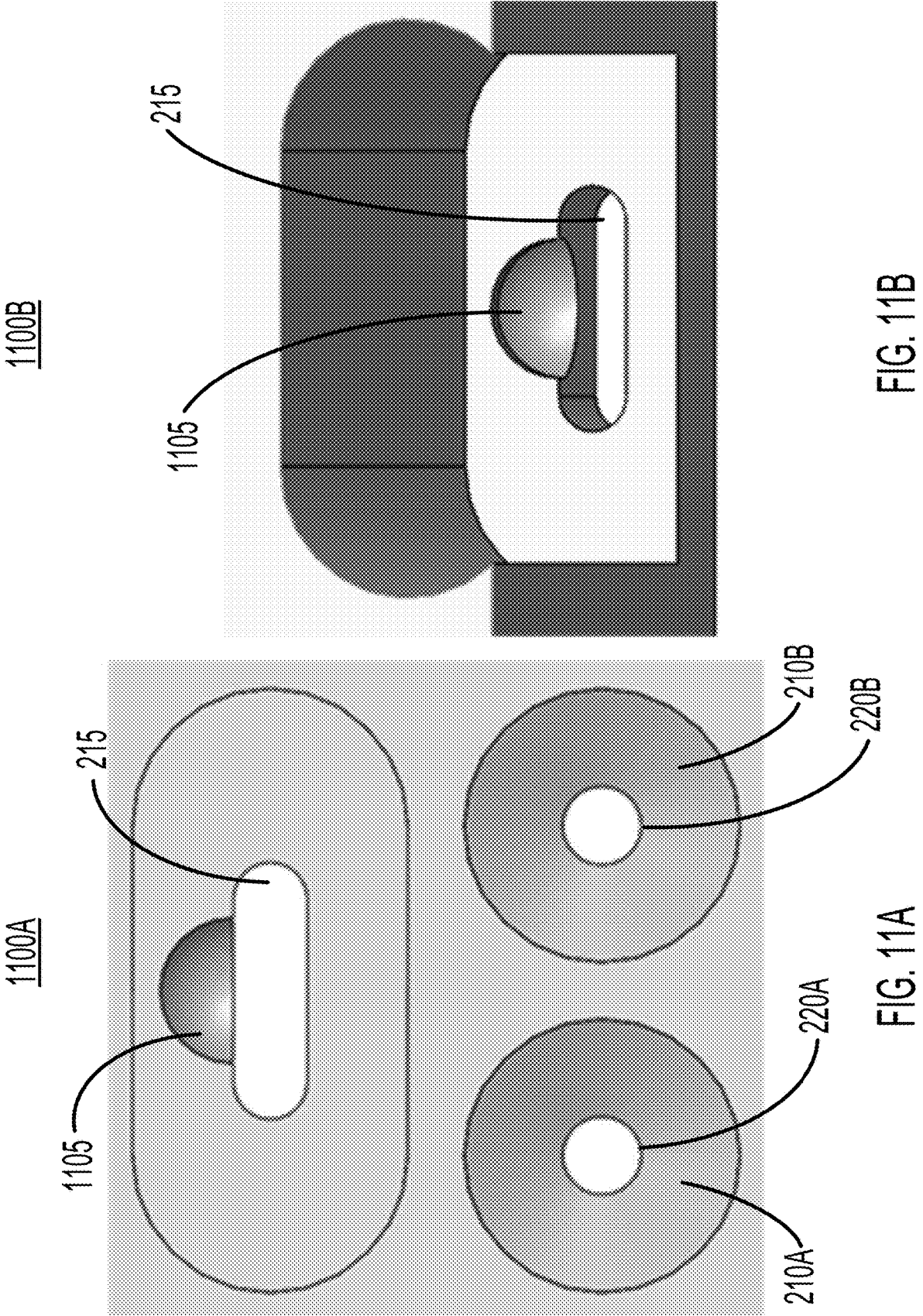
FIGS. 11A and 11B illustrate views of implementations of the microfluidic device shown in FIGS. 2A, 2B, and 2C, with an integrated divot feature, in accordance with one or more implementations.

Referring now to FIGS. 11A and 11B, illustrated is a top view 1100A and a cross-sectional view 1100B of an example implementation of the microfluidic device 110 described herein with an integrated divot feature 1100, in accordance with one or more implementations. As shown, the microfluidic device 110 can include multiple ports, including the culture chamber 215, and two inlet ports 210A and 210B, as described in greater detail herein above in connection with FIGS. 2A and 2B. As described above, the openings 220A and 220B can be coupled to one or more of the well reservoirs 210A and 210A, or the openings 220A and 220B can be formed as a part of the well reservoirs 210A and 210A of a culture plate 105. In addition, the culture chamber 215 can include the divot feature 1105. The divot feature 1105 can be defined in the chamber layer 325. In some configurations, the divot feature 1105 can be added to one or multiple edges of the culture chamber 215 or the step feature 1005 (described herein above in connection with FIGS. 10A and 10B) to improve working access to the culture chamber 215 via pipet tip or other means. The divot feature 1105 can be used to add or remove liquid (including media and cell suspensions) to the culture chamber without disrupting the tissue directly.

Figures 12A, 12B:
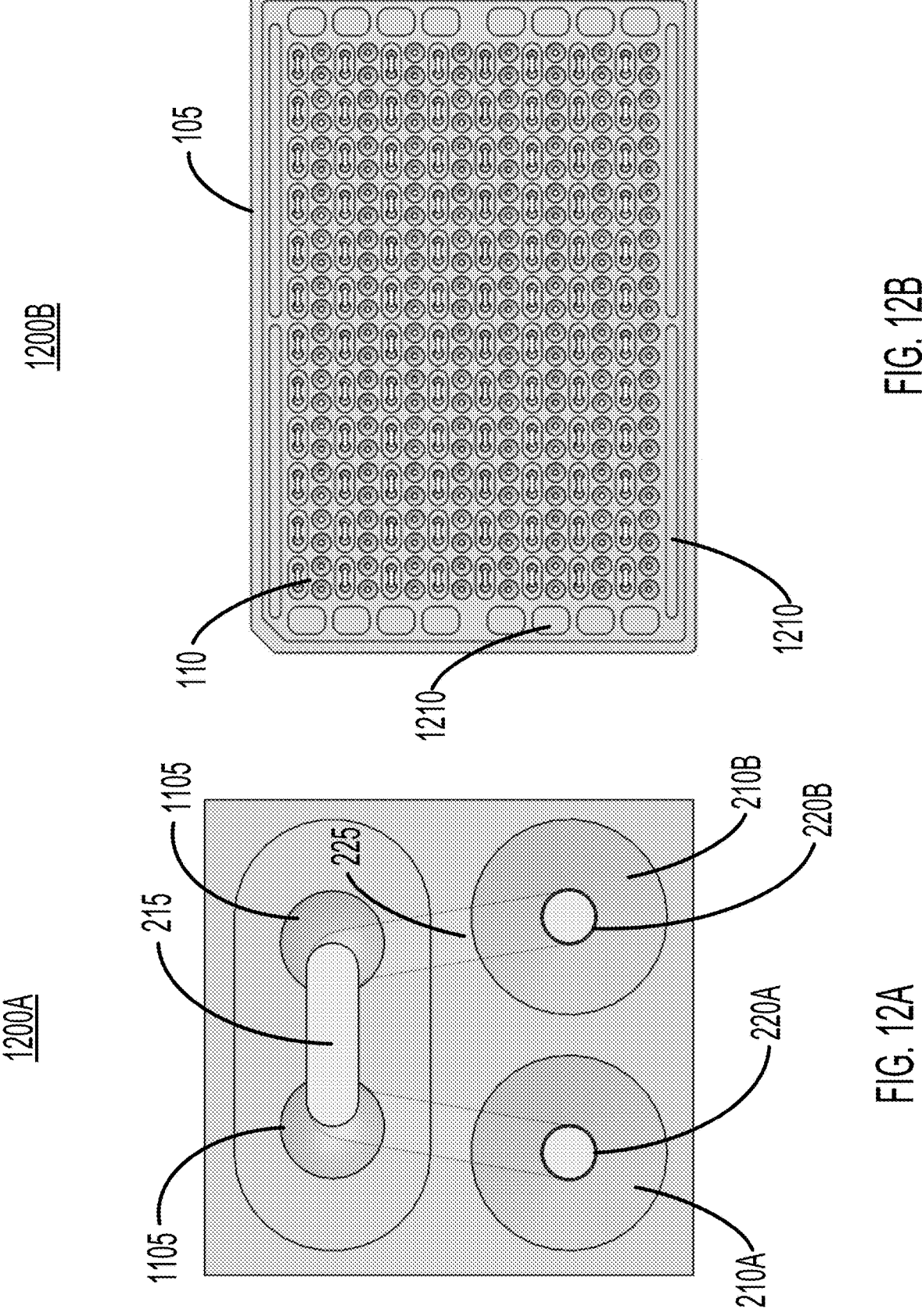
FIG. 12A illustrates a top view of an implementation of the microfluidic devices shown in FIGS. 11A and 11B with two integrated divot features, in accordance with one or more implementations.
FIG. 12B illustrates a top view of an implementation of the well plate illustrated in FIGS. 1A and 1B having a dual divot design and evaporation barrier wells, in accordance with one or more implementations.

An example of a dual divot feature is shown in FIG. 12A. In FIG. 12A, illustrated is a top view 1200A of an implementation of the microfluidic devices 110 shown in FIGS. 11A and 11B with two integrated divot features 1105, in accordance with one or more implementations. As shown, the divot features 1105 can be formed in the chamber layer 325, and can be positioned on either end of the culture chamber 215. However, it should be understood that the divots 1105 can be arranged about the perimeter of the culture chamber 215 in any pattern or position. Further, in some implementations, the microfluidic device 110 can include both the step feature 1005 described herein in connection with FIGS. 10A and 10B and the divot 1105 described herein in connection with FIGS. 11A, 11B, and 12A. In addition, any number or configuration of the microfluidic devices 110 can be defined within a well plate 105. For example, referring now to FIG. 12B, depicted is top view of the example well plate 105 with integrated microfluidic devices 110 having the dual pivot feature 1105 configuration shown in FIG. 12A. In addition, the well plate 105 can include one or more evaporation barrier wells 1210 around the edges of the well plate 105. The evaporation barrier wells 1210 can be filled with fluid to prevent excess evaporation from the perimeter culture wells of the microfluidic devices 110. Particular configurations of coupling the microfluidic device 110 to the well plate 105 are described herein in connection with FIG. 3A.

Referring back now to FIG. 3A, the coupling layer 330 can be a layer of material that facilitates coupling the chamber layer 325 to the well reservoirs 305. As described herein, any openings in the culture plate can be formed using, for example, an ultra-violet (UV) laser system to cut laser-cut thin films of material, such as cyclic olefin polymer or cyclic olefin copolymer. Each layer in the microfluidic device 110 (e.g., the base layer 310, the channel layer 315, the chamber layer 325) can be adhered together, for example, using low-glass transition temperature cyclic olefin copolymer in a heated hydraulic press. The coupling layer 330 can be an adhesive layer. In some implementations, the coupling layer can be laser-cut in the pattern of the well reservoirs 305 to which the microfluidic device 110 will be coupled. The coupling layer 330 can be, for example, a 0.135 mm thick pressure sensitive adhesive. In some implementations, the coupling layer 330 can include a 25.4 um polyester carrier film with MA-69 acrylic medical grade adhesive. The coupling layer 330 can couple the chamber layer 325 to the well reservoirs 305.

The well reservoirs 305 can be similar to, and form a part of, the culture plate 105 described herein above in FIGS. 1A and 1B. As shown, the well reservoirs 305 can include openings that form the well reservoirs 220A and 220B described herein above in connection with FIGS. 2A and 2B. The openings well reservoirs 305 can align with the openings 210A and 210B formed by the openings in the membrane layer 320 and the chamber layer 325, and can align with the culture chamber 215 opening formed in the chamber layer 325. Thus, the well reservoirs 305 can allow for introduction of fluid and cell cultures via the openings 220A and 220B, and can expose the culture chamber 215 to open air, or optionally a fluid if a fluid is provided to the well reservoir 305 positioned above the culture chamber 215. In some implementations, the chamber layer 325, coupling layer 330, and the well reservoirs 305 can be combined into or formed as a single part and made via micromachining, injection molding, or other means. A perspective view 300B of an assembled microfluidic device is shown in FIG. 3B.

Figure 3B:
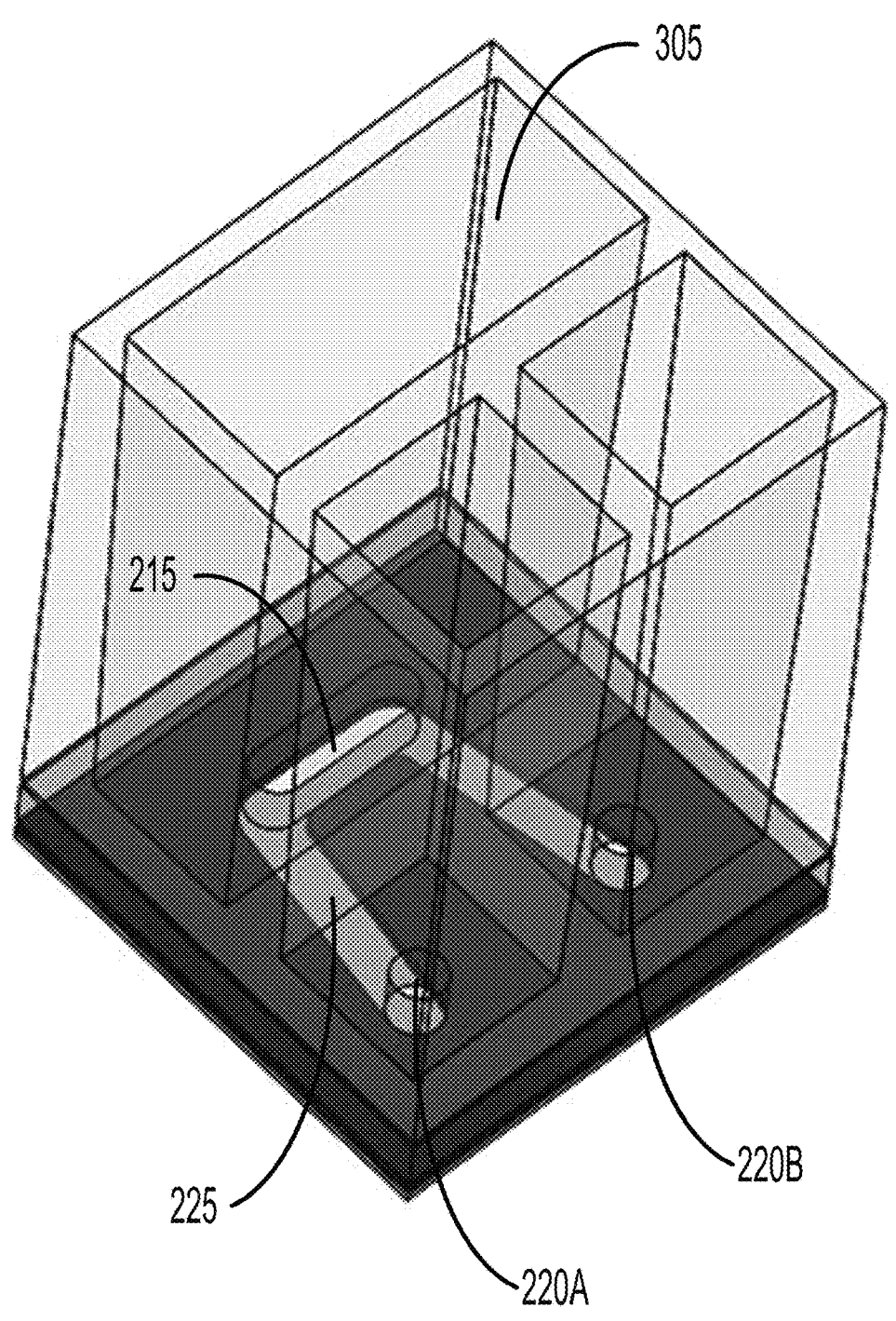

Referring now to FIG. 3B, depicted is a perspective view 300B of an assembled microfluidic device 110 shown in the exploded view 300A in FIG. 3A. As shown, the assembled device can define each of the openings 220A and 220B and the culture chamber 215, each described herein above in connection with FIGS. 2A and 2B. Each of the well reservoirs 305 can align with a respective opening 220A or 220B, or with the culture chamber 215. The microfluidic channel 225 can be fluidly coupled to the culture chamber 215 via the porous membrane in the membrane layer 320. Although the microfluidic device 110 shown in FIGS. 3A and 3B are shown as a single microfluidic device, it should be understood that multiple devices can be defined in each layer shown in FIG. 3A to create an array of microfluidic devices 105 as shown in FIGS. 1A and 1B.

In some implementations, the application of air or fluid flow through an auxiliary system in the lid of the culture plate 105 can align the growing and differentiating cells and tissue. In other embodiments where the culture chamber is fluid filled, the auxiliary pumping system could provide mixing of media and deliver oxygen and nutrients to the tissue through convection. To enable electrical evaluation of the tissue, the culture chamber 215 can have conductive traces or other electrically conductive elements (e.g., formed in or positioned on the chamber layer 325, etc.) that attach to electrical measurement instruments such as a transepithelial electrical resistance measurement device, potentiostat, or voltmeter. The traces would extend to where they would contact the tissue or contact any liquid or moisture that would reside above the tissue sample. This would create a circuit allowing interrogation of the tissue for electrical impedance.

The systems and method of the present solution can be used to create organ-on-chip and tissue models with an air-liquid interface, as well as be used for growth of multi-layer cultures, 3D printed tissues, spheroids, and organoids. The open nature of the culture chamber 215 can enable seeding cells that do not dissociate into single-cell suspensions easily or placing of pre-formed pieces of tissue. Further experimental details of implementations of the systems and methods of the present solution are described herein below.

Normal Human Bronchial Epithelial Cells (NHBEs) were provided for the experiments described herein. To proliferate and cryopreserve stocks of each NHBE donor, cells were thawed and plated at 2500 cells/cm^2 on 804G media coated tissue culture flasks (804G media), cultured in a medium, and passaged using a cell detachment solution. After two passages, NHBEs were cryopreserved using 65% FBS, 25% Bronchialife, and 10% DMSO. To prepare the culture plates 105 for seeding, plates and corresponding pumps were treated with ethylene oxide overnight for sterilization, followed by 120 seconds of plasma treatment. After plasma treatment, culture plates 105 were washed briefly with 70% ethanol, then distilled water, and finally coated overnight in 804G media. To seed culture plates 105 plates, NHBEs were thawed, counted, resuspended in SAGM+4i media (Lonza media, Sigma small molecules, ref for SAGM+4i media), and plated at 10,000 cells per device in a 3 uL volume directly onto the membrane (e.g., the semipermeable membrane of the membrane layer 320, etc.). After 48 hours of growth in SAGM+4i media, differentiation was initiated using HBTEC-ALI media (Lifeline Cell Technology) plus penicillin/streptomycin (Sigma). After 48 hours of submerged differentiation, ALI was initiated by aspirating media from the surface of the tissue in the upper chamber, while 60 uL of fresh media was added to the bottom chamber. Pumping was initiated at 1 uL/min in the bottom channel, and media was changed daily thereafter.

The example system described herein below, and any components thereof, should be understood to be a non-limiting example of the foregoing systems, devices, or methods. Any references to prior-described components are provided as examples, and any limitations provided below should not be considered limiting upon the features described above.

The system used to perform the experiments described herein is organ-on-chip platform comprising: the culture plate 105 with 96 individual microfluidic devices 110, a perfusion system driven by 192 microfluidic pumps in the culture plate 105 lid, and a trans-epithelial electrical resistance (TEER) measurement system. Each microfluidic device 110 in the culture plate 105 can be formed from a 2×2 array of standard 384 wells, with the wall between the top two wells removed to create an asymmetric 3-well cluster. This configuration is shown in FIGS. 3A and 3B. A slotted hard plastic microwell (e.g., the chamber layer 325, here having a 0.864 mm height, 1 mm width, 2 and 0.5 mm length) was positioned in the center of the large well of the well reservoirs 305, with a microfluidic channel (e.g., the channel 225, here having a 0.25 mm height, and 1 mm width) aligned underneath that was connected to the two remaining wells in each microfluidic device 110. The microfluidic channel 225 was capped below with a thin optically clear layer (e.g., the base layer 310). A microporous membrane (e.g., the membrane layer 320, etc.) was used to separate the microwell from the microchannel to allow for the establishment an air-liquid interface.

To fabricate the culture plate 105, a UV laser system (Protolaser U4: LPKF Laser and Electronics, Garbsen, Germany) was used to laser-cut thin films of cyclic olefin polymer (ZF14-188: Zeon Corp., Tokyo, Japan) and cyclic olefin copolymer (8007 COC: Tekni-plex, Wayne, PA, USA). The COP layers can be adhered together using low-glass transition temperature COC in a heated hydraulic press (Carver Inc., Wabash, IN, USA), and can be separated with a 24 µm-thick track-etched polycarbonate membrane with pore diameter of 1 µm (it4ip S.A., Louvain-la-Neuve, Belgium) patterned with an array of holes to provide fluidic access ports to the bottom channel. The microfluidic stack can be attached to a modified 384-well COP plate (Aurora Microplates, Whitefish, MT, USA) using a 0.135 mm thick pressure sensitive adhesive consisting of a 25.4 um polyester carrier film with MA-69 acrylic medical grade adhesive (ARcare® 90106), which can be previously laser-cut in the pattern of the well plate grid and laminated with a hydraulic press at 1.0 MPa for 2 min.

In order to establish recirculating flow in the channels 225, a self-priming micropump array was incorporated into a lid of the culture plate 105 that fluidically interfaces with the culture plate via stainless steel tubes. By pneumatically actuating a pair of valves and a pump chamber independently within each of the 192 micropumps, media can be transferred between the well reservoirs 305 linked by the bottom channel and established a hydrostatic pressure differential, inducing flow through each channel 225. In the culture plate 105, 96 pumps can be active to control perfusion flow through the bottom channels 225 of the device. The micropumps can be configured to operate across a variety of scenarios, including operating continuously or nearly continuously (e.g., continuously exchanging media at a predetermined rate, etc.), or operating according to predetermined time periods. In some implementations, the micropumps or pumps described herein can provide fluid to the channels 225, but cease operation thereafter during cell culturing.

The pneumatic and fluidic manifolds of the micropump array can be constructed via laser-micromachined Ultem polyetherimide and Kapton polyimide films (McMaster-Carr, Elmhurst, Illinois USA) laminated in a heated hydraulic press with phenolic butyral thermosetting adhesive film (R/flex 1000, Rogers Corp., Chandler, Arizona, USA). Fluidic tubing (21G 316L stainless steel hypodermic tubes: New England Small Tube Corp., Litchfield, NH, USA) were glued into the assembly using 353NDPK Hi-Temp Epoxy (Thorlabs, Newton, NJ, USA).

In order to quantify barrier function, TEER can be periodically measured during the ALI differentiation of the NHBE tissues for the culture plate 105. TEER can be measured using an Epithelial Volt/Ohm Meter (World Precision Instruments). Blank TEER values can be established for each device prior to seeding of NHBEs in each device by adding 100 uL of NHBE media to each channel 225. Prior to reading tissue TEER, tissues can be incubated at 37 C for one hour in Hank's Balanced Salt Solution (HBSS) in order to wash any secreted mucus away to avoid its interference with TEER reading. After reading TEER values from each device at each time point (generally, 7, 10, 14, 17, and 21 days of culture), TEER in ohms*cm^2 can be calculated by subtracting the blank read for each device from the raw reading, then multiplying by the membrane area (e.g., 0.037 cm^2).

To prepare tissues for influenza infection, a mucus wash using HBSS as described above was performed for one hour. Viral strains were thawed on ice, and proper dilutions to reach the relevant multiplicity of infection (MOI) were performed using HBTEC-ALI media. When the mucus wash was completed, influenza inoculum can be added to the tissues. Each experiment below can include both a) an untreated control in which ALI was maintained, and b) an untreated control that was submerged in HBTEC-ALI media for comparison to the influenza-treated groups. The time of incubation varied by strain, but was either one or six hours.

After the incubation time was completed, both the top chamber and the bottom channel were aspirated, with complete aspiration of the top chamber to resume ALI culture. 60 uL of HBTEC-ALI was added to the bottom channel to resume normal culture conditions. At both 24 and 48 hours post-infection, a mucus wash using HBSS was performed to collect both mucus and virus. In order to collect RNA from certain devices at either 24 or 48 hours, RLT buffer with betamercaptoethanol (Qiagen) was added to both the top chamber and bottom channel and pipetted vigorously to disrupt the differentiated NHBE tissue. To fix tissues at the 48-hour time point for immunofluorescence staining, tissues were incubated with 4% paraformaldehyde (Sigma) for 10 minutes, then washed three times with HBSS.

Viral supernatant RNA was extracted using a QIAamp Viral RNA Mini Kit (Qiagen) following the manufacturer's instructions. Supernatant volumes of 100 μl were brought to 140 μl using HBSS. Tissue RNA was extracted using an RNeasy Micro Kit (Qiagen) per the manufacturer's instructions. One-step qRT-PCR was then performed using a QuantiTect Probe RT-PCR kit (Qiagen) using the protocol specifications for a QuantStudio 7 Flex RT-PCR system (Applied Biosystems). 7.8 μl of the extracted supernatant viral RNA was used in a 20 μl reaction volume and 3.8 μl tissue RNA was used in a 20 μl reaction volume. Taqman primers and probe targeting IAV-M were ordered from Thermo Scientific with the following sequences: FLUAM-7-F: CTTCTAACCGAGGTCGAAACGTA, FLUAM-161-R: GGTGACAGGATTGGTCTTGTCTTTA, FLUAM-49-P6: TCAGGCCCCCTCAAAGCCGAG. Taqman Gene Expression Assays (Thermo Scientific) were used to target the following proteins in lung tissue: ACE2, TMPRSS2, TUBB6, and Muc5AC. Supernatant viral copies/ml were calculated using a standard curve generated from serial dilutions of A/PR/8/34 viral RNA. Fold change in expression of the target genes in lung tissue were determined by calculating the $\Delta\Delta Ct$ after normalization to the housekeeping gene GAPDH.

Figure 4A:
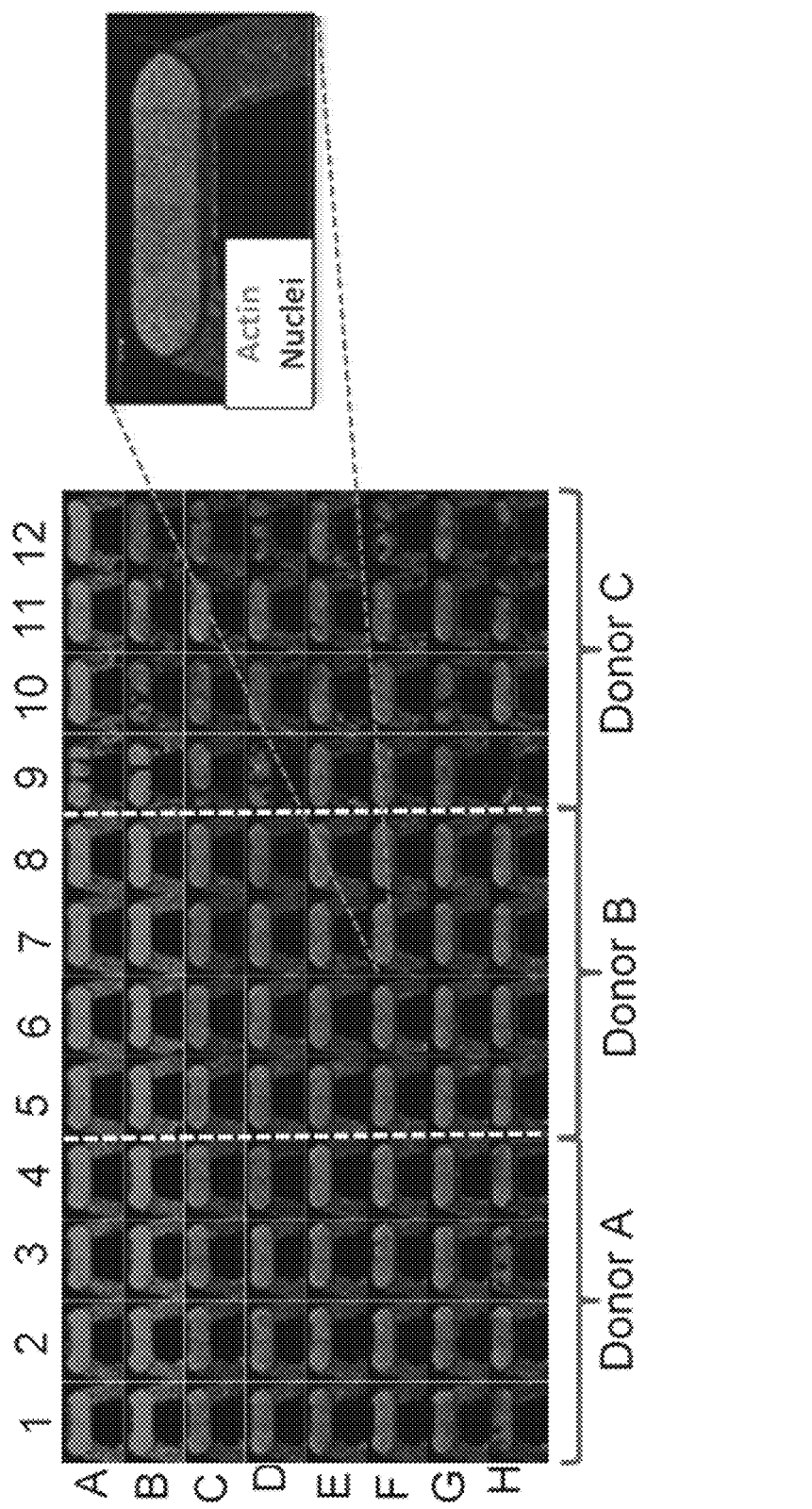
FIG. 4A depicts actin and nuclear staining of wells in the well plate illustrated in FIGS. 1A and 1B, in accordance with one or more implementations.
Figure 4B:
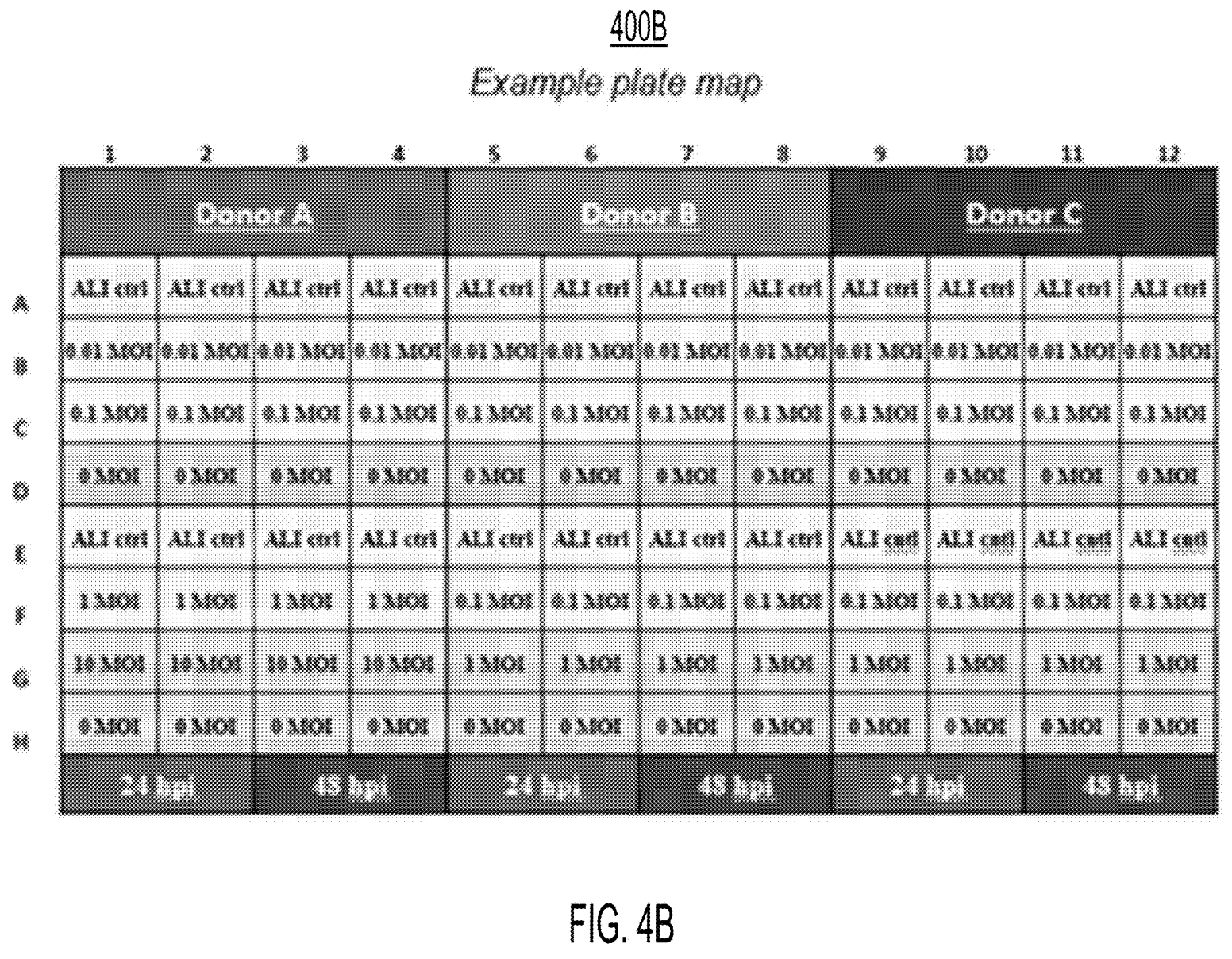

In FIGS. 1A and 2B, shown is a culture plate 105 used in the organ-on-chip system described above for the ALI model, with the opportunity to inoculate cultured tissues in each well apically or basally and to sample the basal media at regular intervals and examine the tissues at the completion of each study. FIG. 4A illustrates an image 400A of actin and nuclear staining of each of the 96 wells, with all 8 rows and groups of 4 columns utilized for an experiment with a particular lot of donor cells. In FIG. 4B, depicted is a table 400B indicating a plate map that shows the capacity of the 96-well plate to house replicates (4 per condition) for each of three donor populations, across two time points and 4 MOIs. The experimental design could be varied in many ways, including replacing the donor variable with a test of three different therapeutics on the plate within a single donor cell population.

Figure 5A:
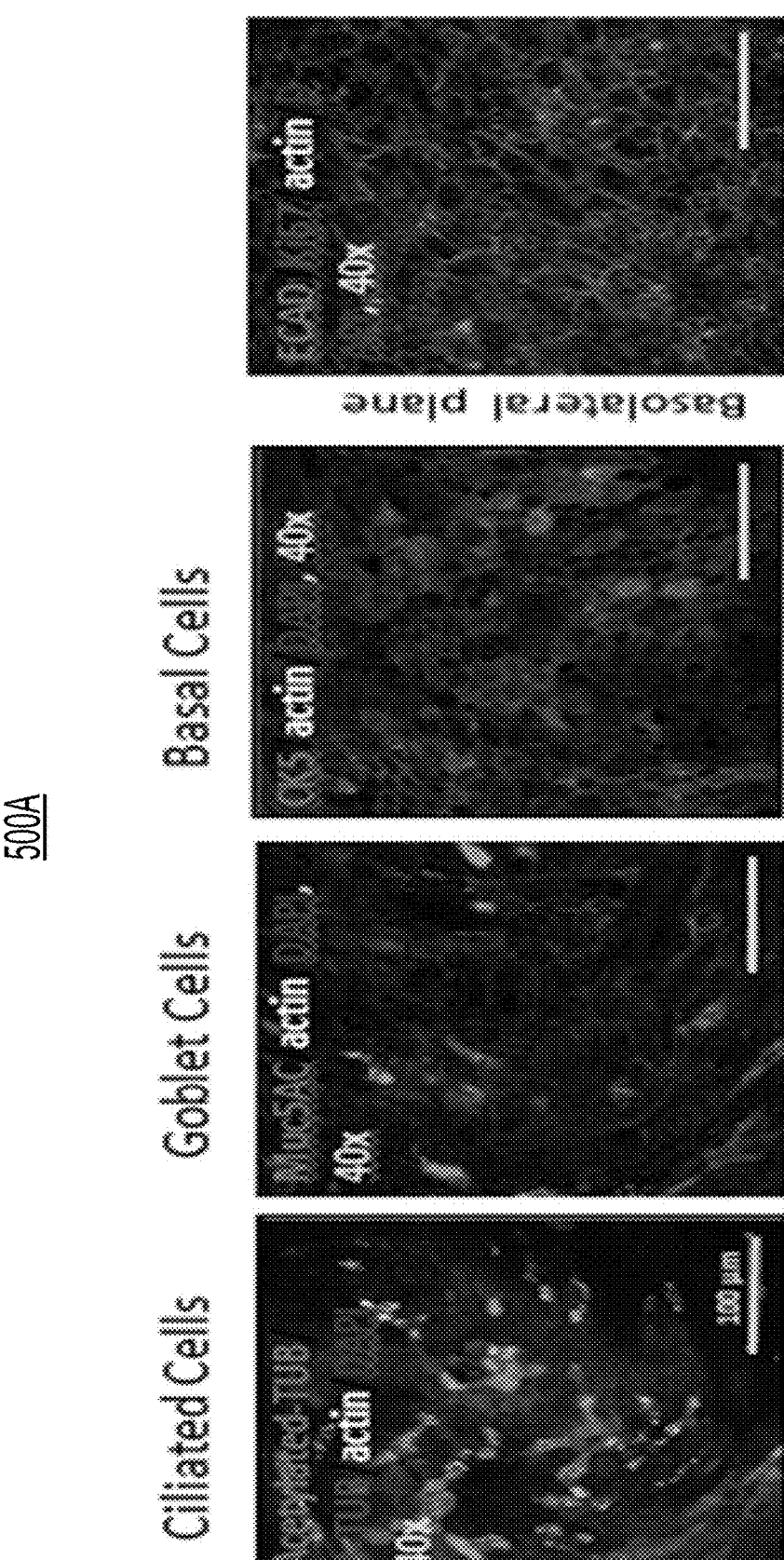
FIG. 5A depicts staining of ciliated cells, goblet cells, and basal cells, in accordance with one or more implementations.

First, the organ-on-chip system including the culture plate 105 was used to establish the healthy baseline airway model, prepared as described above, and morphology and cell populations were evaluated using high resolution confocal microscopy and immunohistochemistry. In FIG. 5A, shown is a set of images 500A including staining of ciliated cells, goblet cells, and basal cells. In FIG. 5B, shown is a cross-sectional view 500B of the pseudostratified epithelial layer comprising 4-6 monolayers. In FIG. 5C, shown is a graph 500C of TEER measurements for three different donor populations of NHBEs across 30 days of ALI culture, rising to approximately 1000 $\Omega cm^2$ after 21 days in culture. These TEER measurements are comparable to levels seen in vivo physiological levels.

Figure 6A:
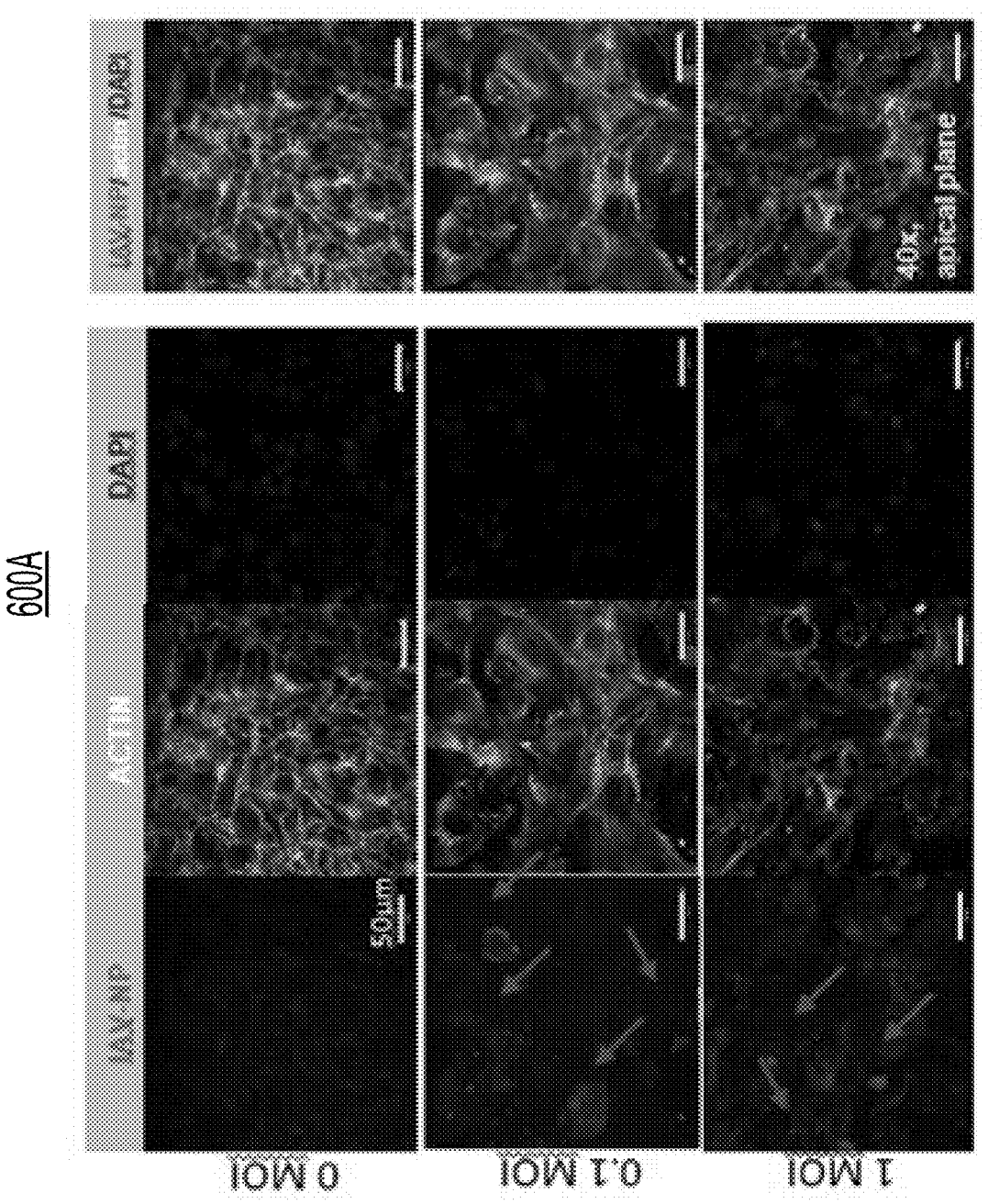
FIG. 6A depicts immunofluorescence staining of air-liquid-interface (ALI) culture cells inoculated with various multiplicities of infection (MOI), in accordance with one or more implementations.
Figure 6B:
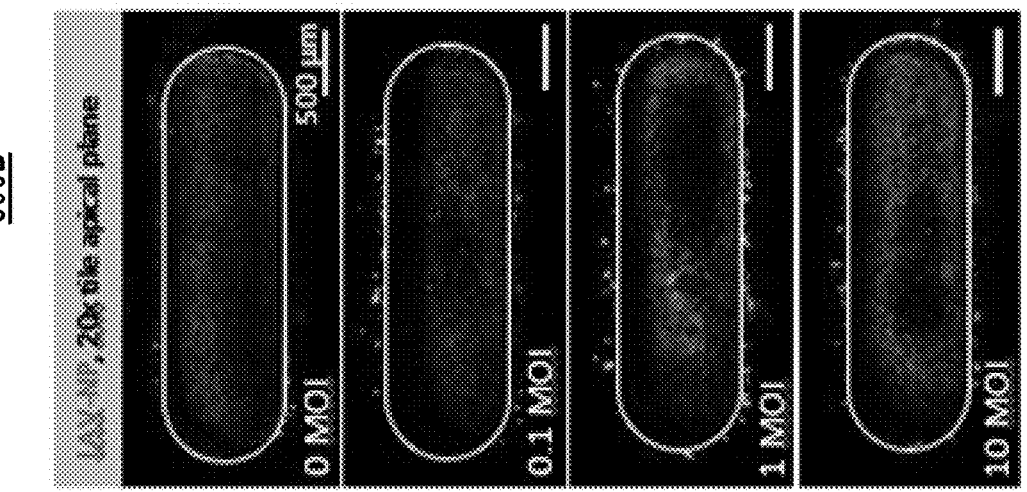
FIG. 6B depicts magnified images at the apical plane showing influenza A virus (IAV) nucleoprotein (NP), in accordance with one or more implementations.
Figure 6C:
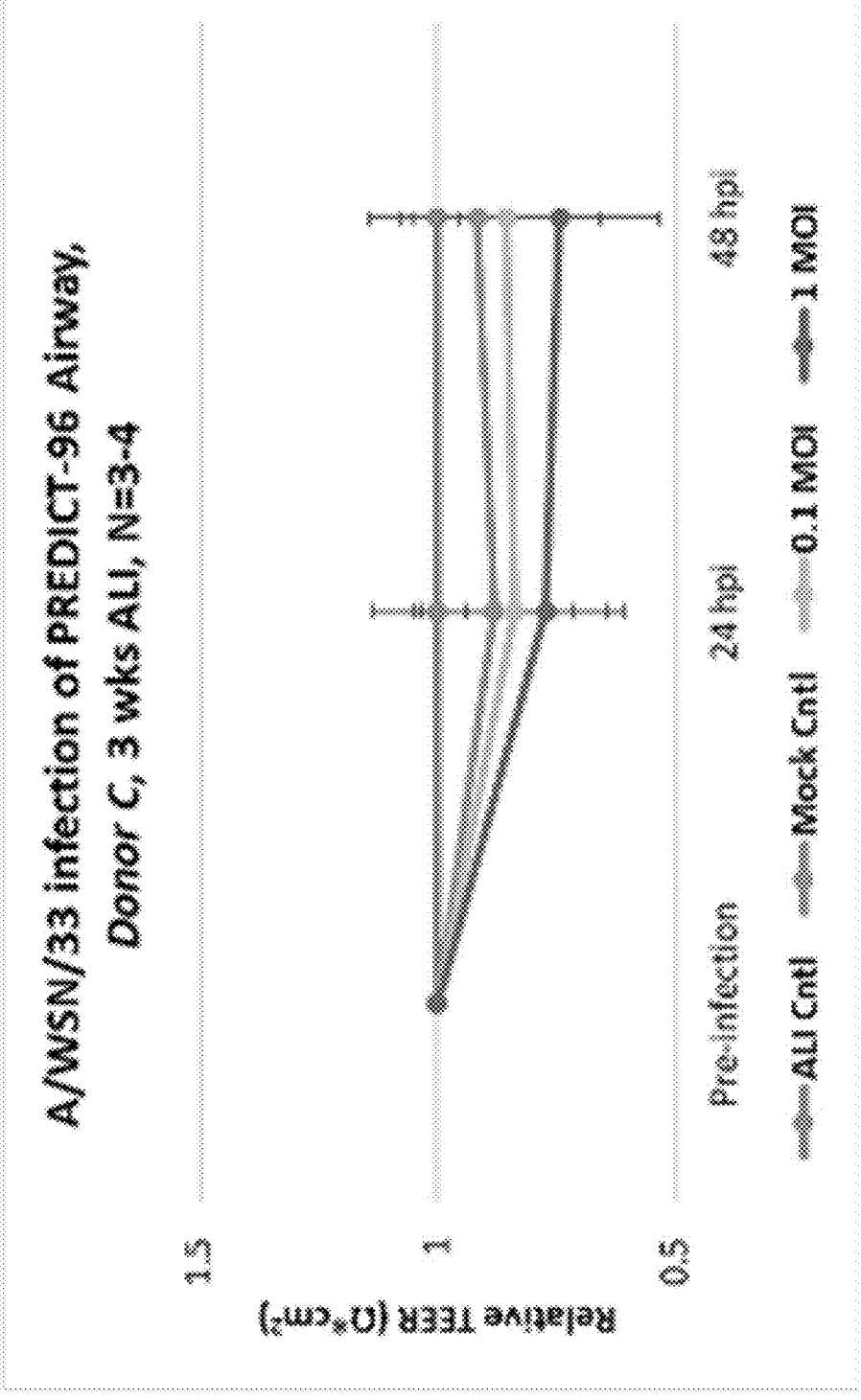
FIG. 6C depicts a graph of normalized TEER levels monitored across pre-infection through 48 hours post-infection, in accordance with one or more implementations.

Next, the effect of inoculation of these ALI cultures with various strains of IAV, including A/WSN/33, A/California/04/09 H1N1 and A/HongKong/8/68 H3N2 is examined. In FIG. 6A, shown are images 600A of immunofluorescence (IF) staining of ALI culture wells inoculated with various multiplicities of infection (MOI) of A/WSN/33 are displayed, exhibiting a higher prevalence IAV NP as the MOI increases. FIG. 6B shows 20× images 600B at the apical plane show IAV NP staining across the range of 0-10 MOI, again exhibiting a significant increase with MOI. Normalized TEER levels monitored across pre-infection through 48 hours post-infection (p.i.) are shown in the graph 600C of FIG. 6C; each line represented triplicate readings of TEER for a particular MOI across the three time points and TEER was normalized to the average value for those three wells prior to infection. TEER values decline at higher MOI as expected; this relationship is investigated across multiple populations of donor cells and have observed that the TEER response to infection is donor-dependent (data not shown.)

Figure 7A:
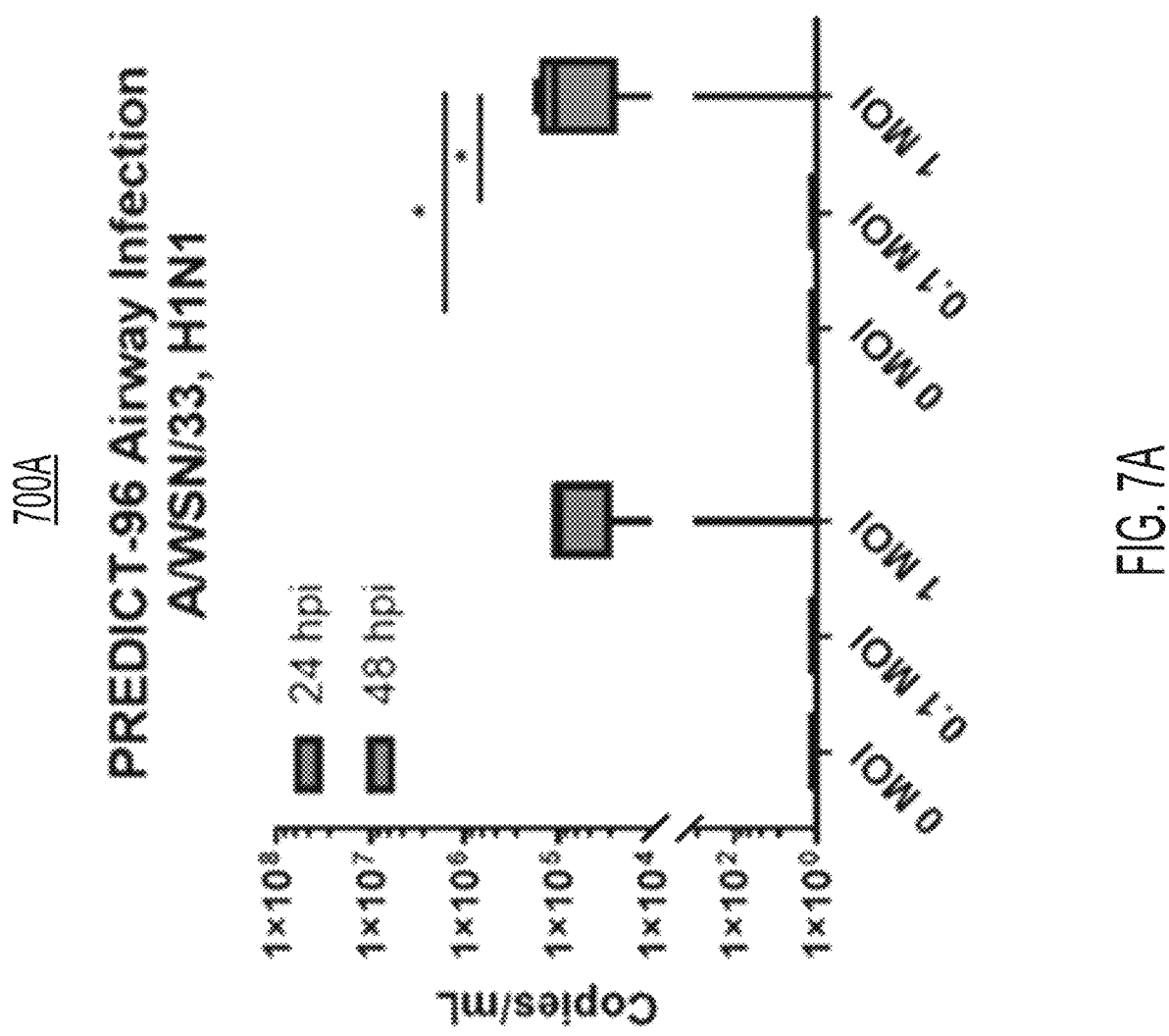
FIG. 7A depicts a graph of viral infection kinetics for A/WSN/33 strain of IAV across a range of MOI, in accordance with one or more implementations.
Figure 7B:
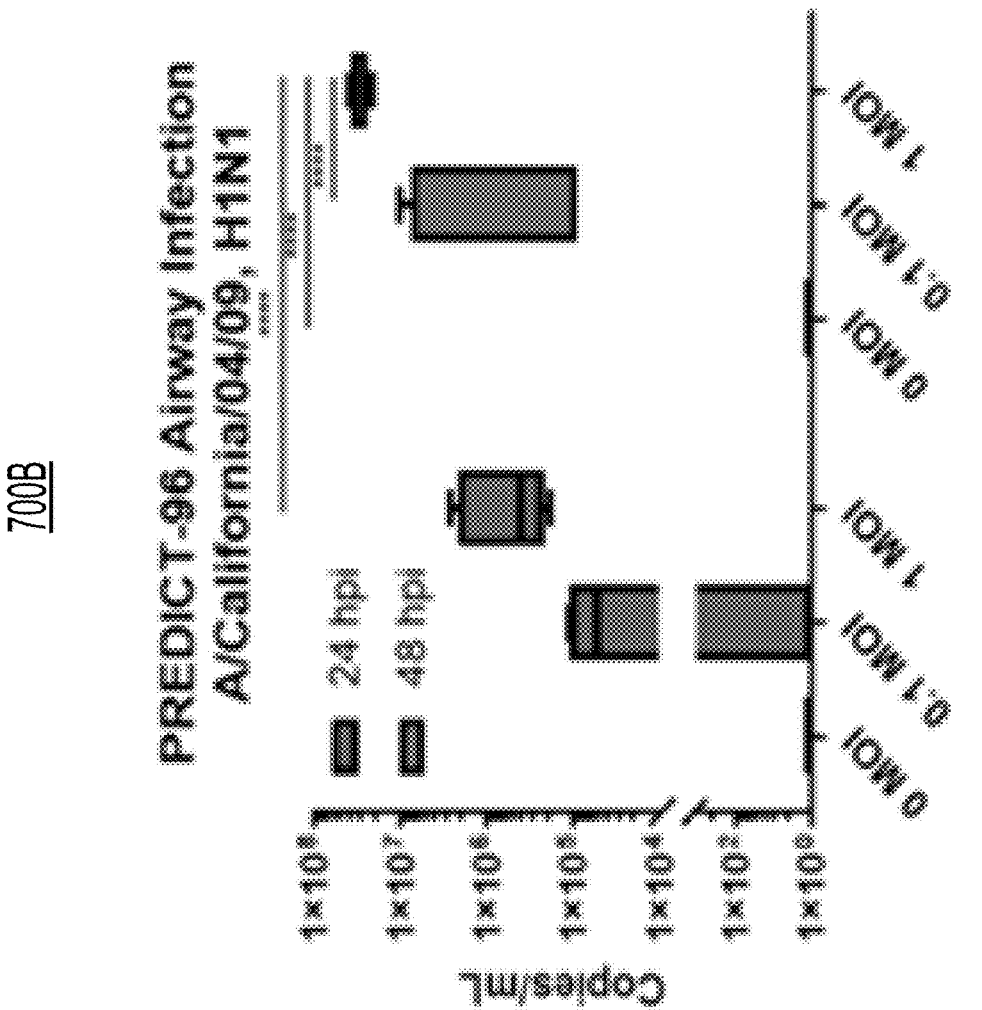
FIGS. 7B and 7C depict graphs of companion results for A/California/04/09 H1N1 and A/HongKong/8/68 H3N2, in accordance with one or more implementations.
Figure 7C:
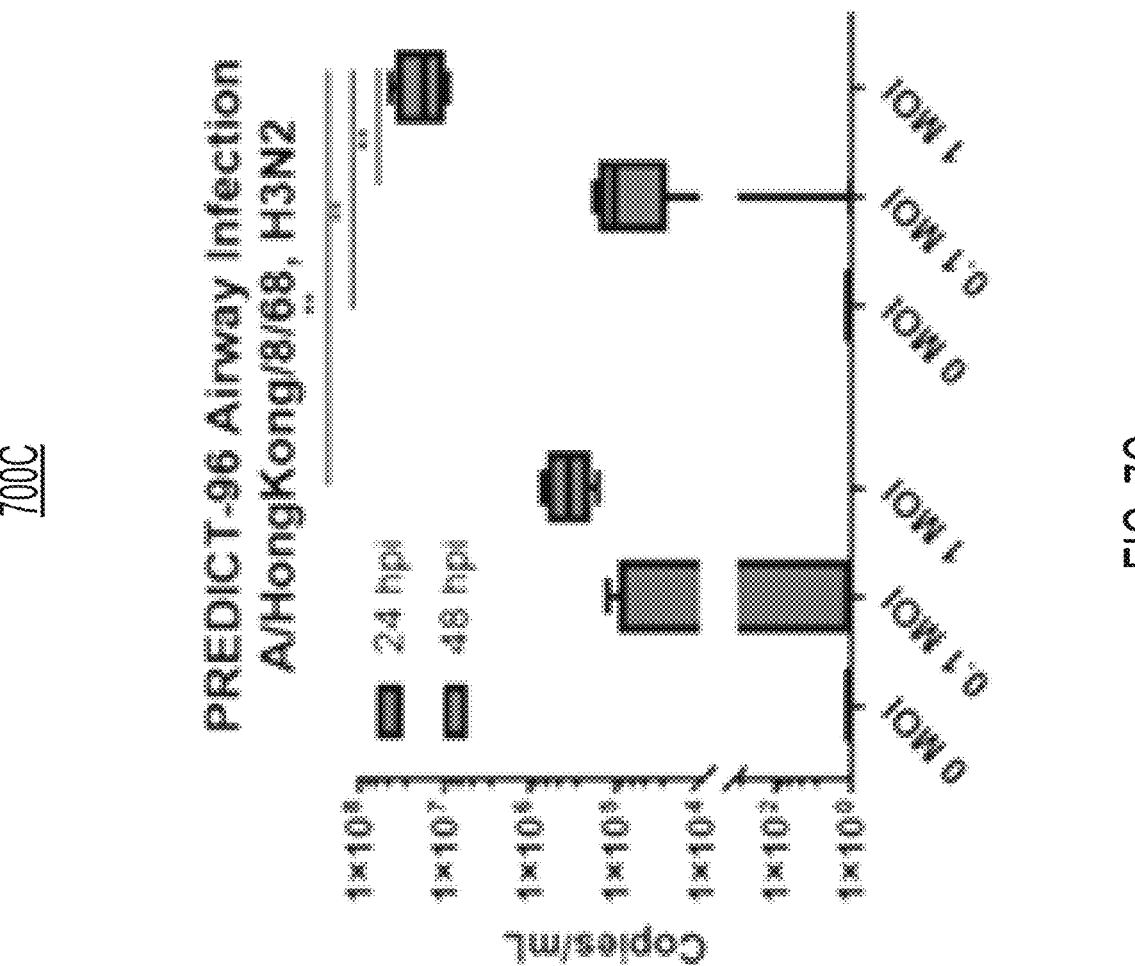

Measurements of viral supernatant RNA were obtained using quantitative reverse transcription polymerase chain reaction (qRT-PCR), and are provided in the three plots in FIGS. 4A, 4B, and 5C. In FIG. 7A, the plot 700A shows viral infection kinetics for the A/WSN/33 strain of IAV, across a range of MOI and two time points p.i. In FIGS. 7B and 7C, depicted are companion graphs 700B and 700C for A/California/04/09 H1N1 and A/HongKong/8/68 H3N2 are shown. For the WSN strain, viral copies per mL show a step function between MOI=0.1 and MOI=1, and are relatively flat after 24 hours p.i. For the H1N1 and H3N2 strains, infection kinetics rise more monotonically with MOI, and continue to increase between 24 and 48 hours p.i.

Figure 8A:
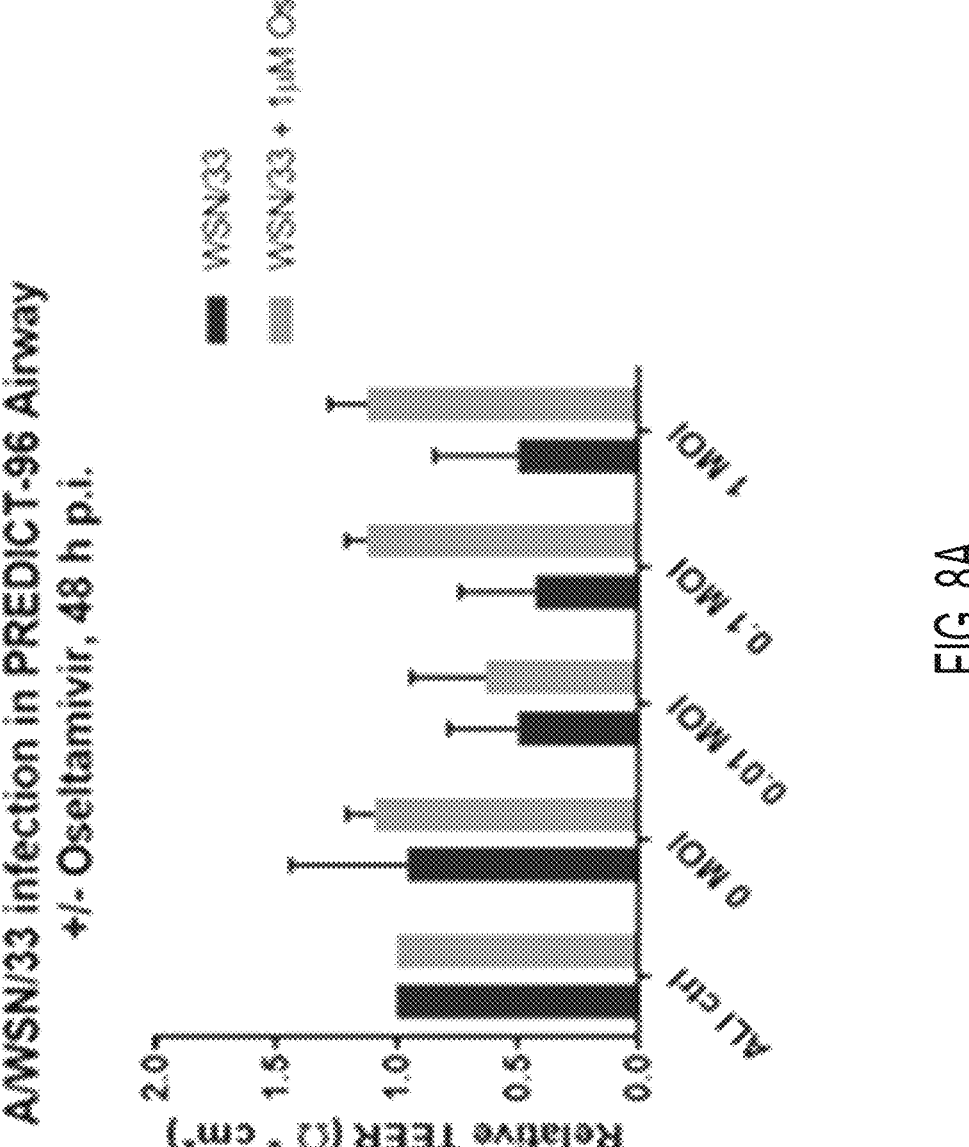
FIG. 8A depicts a graph of the effect of oseltamivir on barrier function, in accordance with one or more implementations.
Figure 8B:
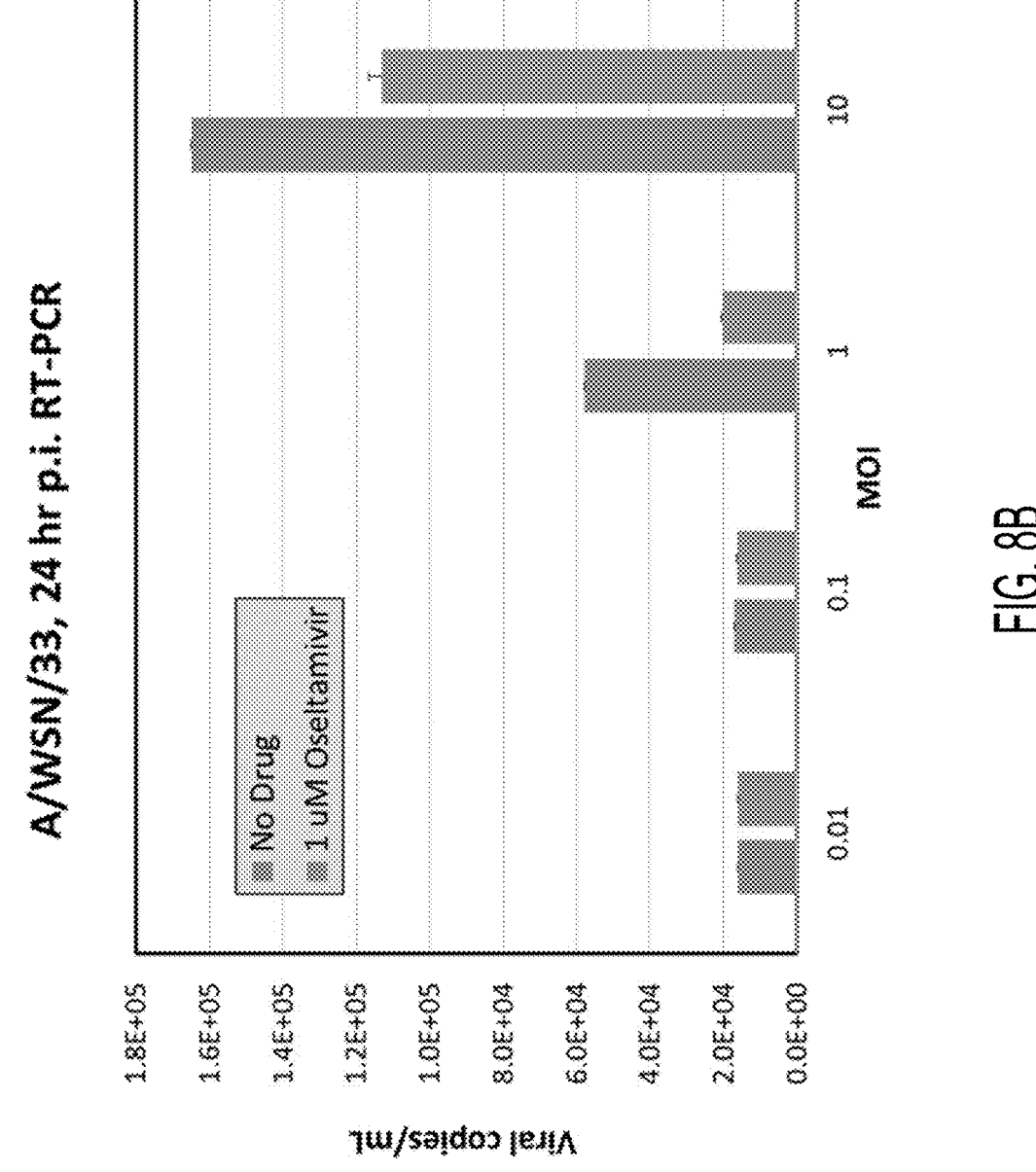
FIG. 8B depicts a graph of infection kinetics for treated and untreated groups of wells for the WSN/33 strain, in accordance with one or more implementations.
Figure 8C:
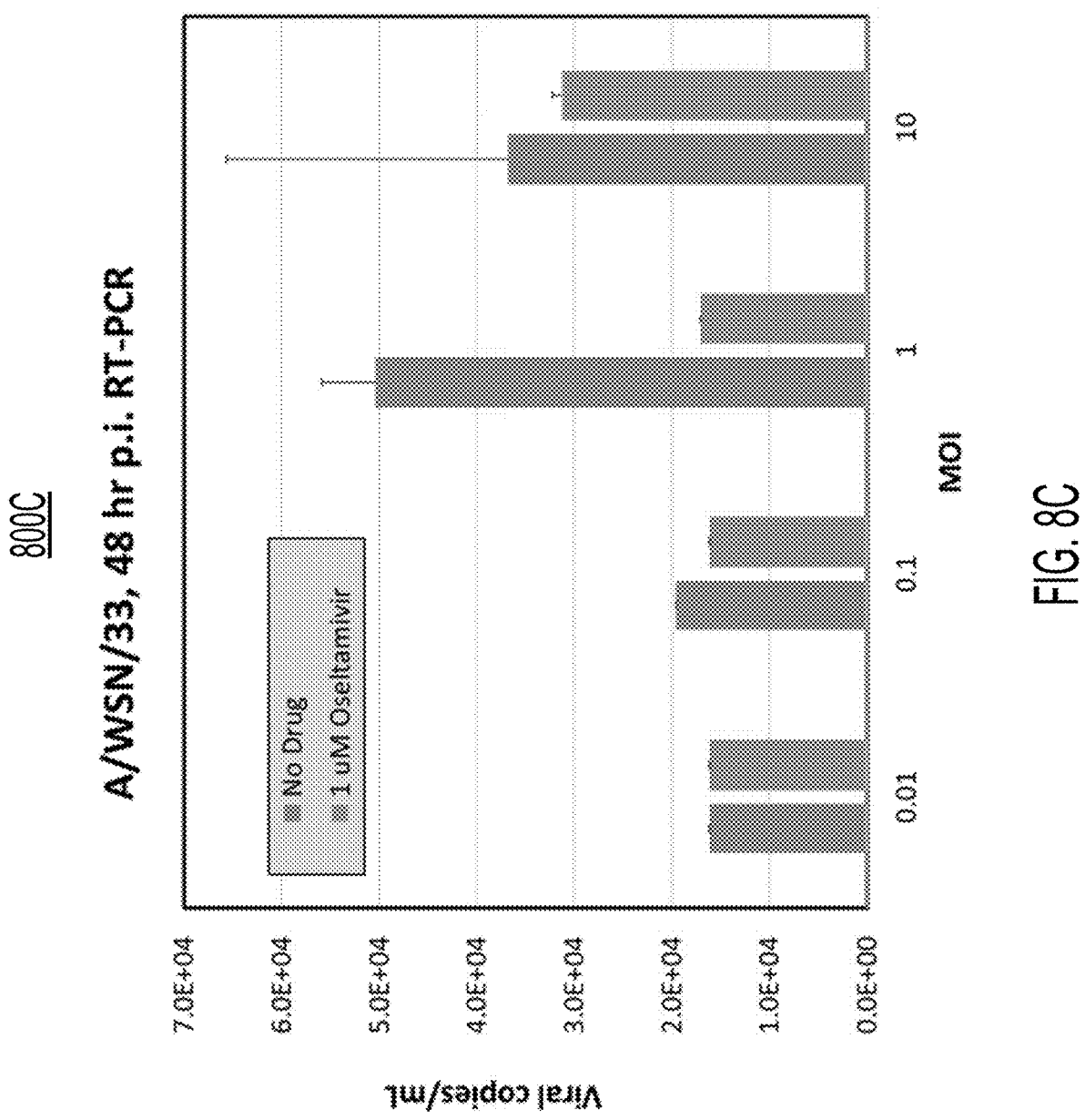
FIG. 8C depicts a graph of infection kinetics for treated and untreated groups of wells for the WSN/33 strain 48 hours post-infection, in accordance with one or more implementations.

Also investigated is the effect of the antiviral agent oseltamivir on the infection kinetics of the A/WSN/33 strain, monitoring both TEER and viral titers with qRT-PCR. FIG. 8A shows a graph 800A of the effect of oseltamivir on barrier function, indicating a protective effect for the agent (orange bars) relative to untreated controls (blue bars) across a range of MOI. The oseltamivir concentration of 1 µM was selected for the WSN strain; literature reports for pandemic strains typically utilize lower drug concentrations. In FIG. 8B, shown is a graph 800B of infection kinetics for treated (orange bars) and untreated (blue bars) groups of wells are shown for the WSN/33 strain 24 hours p.i., while in the graph 800C of FIG. 8C, the 48 hour p.i. data is provided.

Figure 9:
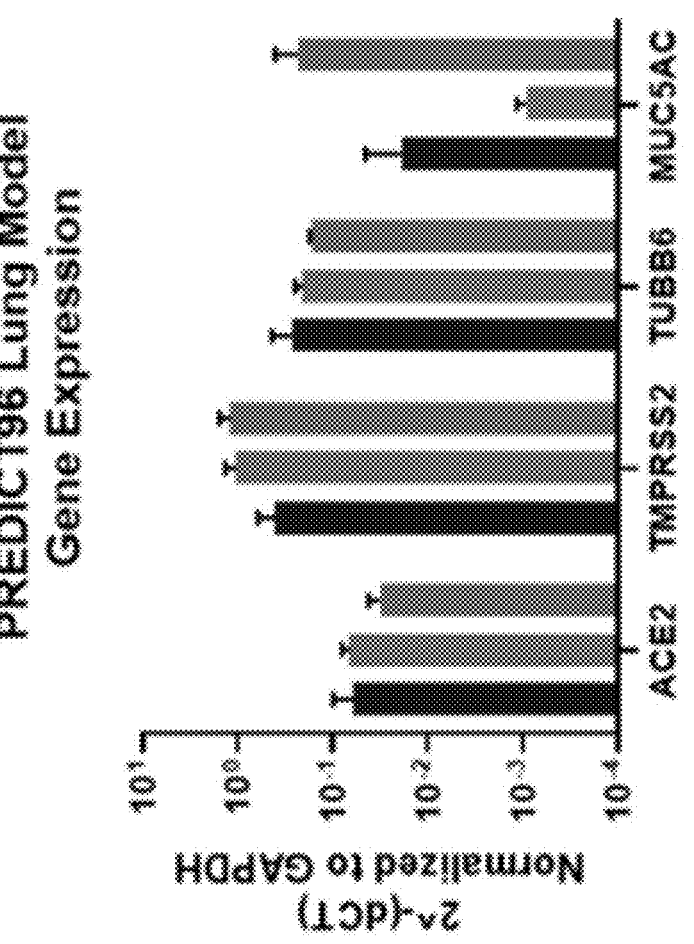
FIG. 9 depicts a semi-logarithmic graph for cell populations derived from three different donors, in accordance with one or more implementations.

Finally, receptors believed to play central roles in another respiratory virus, SARS-CoV-2, namely the ACE2, and TMPRSS2 receptors, were probed. This data, along with the cilia cell gene TUBB6 and the secretory cell gene Muc5AC, are plotted on a semi-logarithmic scale in graph 900 of FIG. 9, for cell populations derived from three different donors.

An important need in the field of respiratory virus research is the establishment of robust in vitro disease models that provide the precision, validation, throughput, and utility necessary for routine operation in drug development laboratories. The systems and methods described herein represent the first high-throughput organ-on-a-chip platform with integrated precision flow control and sensing in a standard SBS well plate format. As described herein, the first application of this platform to a barrier tissue model at an air-liquid-interface (ALI) is reported, with human primary tracheobronchial cells establishing a pseudostratified epithelium atop a semipermeable membrane with independent flow control in the apical well and basal channel and in-line real-time TEER sensing, enabling 96 separate experimental conditions on a single standard well plate configuration. This 96-well platform with the capacity to investigate multiple donors, viral strains, MOI, time points, and therapeutic interventions, with replicates, all in a single plate experiment. Data presented demonstrates the ability of this system to establish a robust model for the human airway using primary tracheobronchial epithelial cells, with an appropriate distribution of cell populations, morphology and barrier function for use as the basis of a disease model for IAV.

The model has been deployed to investigate the kinetics of infection of three different strains of IAV; the WSN/33 strain and pandemic strains of H1N1 and H3N2. Infection kinetics are monitored using a combination of IF, in situ TEER, and qRT-PCR, across a range of MOI and time points, providing a robust foundation for evaluation of therapeutic interventions. As a proof of concept, these infected cultures have been treated with oseltamivir, showing a protective effect on barrier function and reduction in viral titers across several MOI and multiple time points. Finally, the potential relevance of this model to coronavirus studies has been demonstrated by confirming the presence of the ACE2 and TMPRSS2 receptors in our ALI culture. This data provides a strong basis to establish the systems described herein as having favorable capability for preclinical evaluation of therapeutics for respiratory infections in an efficient, robust and high-throughput manner.

Further experimental details are explained herein below, in accordance with one or more embodiments described herein.

Currently, in vitro systems for evaluation of therapeutics for COVID-19 rely upon high throughput well plate-based systems cultured with cell lines such as Vero E6, Calu-3 and A549. More recent developments include the use of genetic modification techniques to confer physiologically relevant properties to various immortalized cell lines, induced pluripotent stem cell (iPSc)-based systems, and the development of human primary epithelial cell-based technologies including organoids and various lung on a chip systems. While these latter approaches provide a more physiologically relevant microenvironment for investigating key mechanisms of SARS-CoV-2 infection, they are generally limited in throughput and in the ability to fully integrate into the laboratory infrastructure and pharmaceutical development pipelines. Here we report on the first application of a high throughput organ-on-chip system capable of evaluating coronavirus infection across multiple viral strains and human primary cell donors on a single plate. First we confirm expression of the receptor ACE2 and the serine protease TMPRSS2 in human primary airway epithelial tissues cultured in the ALI system, a key attribute toward modeling infection with HCoV-NL63 and SARS-CoV-2. We demonstrate viral propagation and infection kinetics of HCoV-NL63, which, like SARS-CoV and SARS-CoV-2, utilizes ACE2 as its target receptor. We also evaluate HCoV-OC43 infection in the system across MOI and human donors, providing evidence of the extensibility of the system. Finally, as a proof-of-concept demonstration toward future use of the system in evaluation of therapeutic efficacy of SARS-CoV-2 in the model, we present data on the treatment of HCoV-NL63-infected tissues with camostat mesylate, a protease inhibitor that blocks coronavirus entry.

Each device in the ALI culture plate was formed from a 2×2 array within a standard 384-well plate, with the wall between the top two wells removed to create a 3-well cluster. This configuration is shown in FIG. 1A. In some implementations, FIG. 1A depicts a well plate having a slotted hard plastic microwell (0.864 mm height, 1 mm width, 2.5 mm length) that was positioned in the center of the large well, with a microfluidic channel (0.25 mm height, 1 mm width) and aligned underneath that was linked to the two remaining wells in each device. The channel can be capped from below with a thin optically clear layer. A microporous membrane was used to separate the top microwell from the bottom microchannel to permit the establishment of an ALI.

A self-priming micropump array can be incorporated into the lid that serves as the fluidic interface with the culture plate via stainless steel tubes. The pumping system has 192 individual pneumatically-actuated micropumps embedded in the plate lid: two per culture device, one for the chamber above the membrane and one for below. However, since the upper chamber is at ALI, only the 96 pumps serving the microchannel are in use during these experiments. Actuation of the pumps transfers media between the wells linked by the bottom channel and establishes a hydrostatic pressure differential, inducing flow through each microchannel.

In order to quantify barrier function, trans-epithelial electrical resistance (TEER) was periodically measured during the ALI differentiation of the ALI normal human bronchial epithelial (NHBE) tissues. TEER was measured using an Epithelial Volt/Ohm Meter (World Precision Instruments). Blank TEER values were established for each device prior to seeding of NHBEs in each device by adding 100 µL of NHBE proliferation media to each channel. Prior to reading tissue TEER, tissues were incubated at 37° C. for one hour in Hank's Balanced Salt Solution (HBSS, Sigma) in order to wash away secreted mucus to avoid its interference with TEER reading. After reading TEER values from each device at each time point (generally, 7, 10, 14, 17, 21, 24, and 28 days of culture), TEER in ohms*cm² was calculated by subtracting the blank read for each device from the raw reading, and then multiplying this resistance value by the membrane surface area.

Collection and Preparation of Human Primary Bronchial Epithelial Cells From Healthy Controls Participants were recruited via advertisement in the Massachusetts General Hospital (MGH) outpatient clinics and around the Boston metropolitan area. Healthy volunteers between 18 and 50 years old were screened for eligibility with a full medical history. Subjects gave their written informed consent before testing and sample collection. The study was approved by the MGH Institutional Review Board. Volunteers underwent bronchoscopy with conscious sedation. Bronchoalveolar lavage was performed using 4×30-milliliter (mL) aliquots of normal saline. The bronchial mucosa was then sampled using a 4 mm sterile nylon cytology brush. Brush samples were placed in ice-cold RPMI media with 2% human serum and 10 μM ROCK inhibitor (Y-27632, Tocris Bioscience) and cells were gently removed from the brush using a P1000 pipette tip and serially washed with media. The cell suspension was filtered through a 70 μm filter and centrifuged.

The Culture, Cryopreservation, and ALI Seeding and Differentiation of NHBEs are described below. NHBEs were purchased from Lifeline Cell Technology and Lonza. To maintain stocks of each NHBE donor, cells were thawed and plated at 2500 cells/cm² on 804G media-coated tissue culture flasks (804G media), cultured in Bronchialife (Lifeline Cell Technology), and passaged using Accutase (Sigma). After two passages, NHBEs were cryopreserved using 65% FBS (Thermo Fisher), 25% Bronchialife (Lifeline Cell Technology), and 10% DMSO (Sigma). Prior to seeding, ALI plates were sterilized overnight with ethylene oxide gas followed by one week of outgassing in a vacuum chamber. ALI plates were subsequently treated with plasma for 120 seconds and washed briefly with 70% ethanol, rinsed three times in distilled water, and coated overnight in 804G media. To seed ALI plates, NHBEs were thawed, counted, resuspended in complete small airway epithelial cell growth media (SAGM; Lonza), 100 U/mL penicillin-streptomycin (Thermo Fisher), 5 μM ROCKi (Tocris), 1 μM A-83-01 (Tocris), 0.2 μM DMH-1 (Tocris), 0.5 μM CHIR99021 (Tocris) (hereafter referred to as SAGM+4i), and plated at 10,000 cells per device in a 3 μL volume directly onto the membrane. After 48 hours (h) of growth in SAGM+4i media, differentiation was initiated using fresh HBTEC-ALI media (Lifeline Cell Technology) plus 100 U/mL penicillin/ streptomycin.

After 48 h of submerged differentiation, the ALI was initiated by aspirating media from the apical surface of the tissue in the top chamber, while 60 μL of fresh HBTEC-ALI or custom-ALI media was added to the bottom chamber. Pumping was initiated at 1 μL/min in the bottom channel, and the media in the bottom channel was changed daily thereafter. Tissues were matured over the course of 3-5 weeks in ALI culture prior to viral infection experiments. To remove accumulated mucus from the apical surface of the maturing tissue, 100 μL of 1× Hank's Balanced Salt Solution (HBSS) was added to the apical surface of each tissue and incubated on the tissues for 1 h at 37° C. with rocking, subsequently followed by an additional 5 min wash with 100 μL of 1× HBSS at room temperature every 7 days (d). Mucus washings were pooled, collected and stored at −80° C. until processed. Tissue maturity and quality control was scored by a combination of metrics including barrier function, percent ciliated cells, ciliary beat, mucus secretion, and global tissue morphology, and this score was used to determine if individual devices of ALI airway tissue were suitable for downstream experimentation and viral infection. Downstream processing of tissues following viral inoculation was generally conducted at 4-6 weeks of ALI and included tissue apical washes, basal media collection, measurement of barrier function, harvest of tissue for RNA extraction, and fixation for immunofluorescence (IF) imaging.

Oseltamivir carboxylate (F. Hoffmann-La Roche Ltd., Basel, Switzerland) was used in anti-viral screens performed on ALI tissue. Oseltamivir in distilled water was diluted to 1 μM in complete HBTEC-ALI or custom-ALI media and applied to the bottom channel of ALI airway tissues subject to anti-viral evaluation following the standard apical wash of the tissue and 2 h prior to IAV-inoculation. Upon and after IAV-inoculation of the apical side of the ALI tissue, 1 μM oseltamivir was maintained in the basal media for the duration of the study. Basal media changes including oseltamivir occurred every 24 h.

Camostat mesylate (R&D Systems, BioTechne Corp., Minneapolis, MN) was used on ALI tissue infected with coronavirus strain HCoV-NL63. Camostat mesylate in DMSO was diluted to 20 μM in complete HBTEC-ALI or custom-ALI media and applied to the bottom channel of ALI airway tissues subject to anti-viral evaluation following the standard apical wash of the tissue and 2 h prior to HCoV-NL63 inoculation. Upon and after HCoV-NL63 inoculation of the apical side of the ALI tissue, 20 μM camostat mesylate was maintained in the basal media for the duration of the study. Basal media changes including camostat mesylate occurred every 24 h.

To prepare ALI tissues for influenza and coronavirus infection, a mucus wash with 1× HBSS was performed as described above. Viral strains were thawed on ice and individually diluted in viral infection media to reach the relevant MOI. Influenza virus infection media was composed of a single IAV strain diluted to the appropriate MOI in HBSS including 1 μg/mL TPCK-trypsin (Sigma) for A/California/04/09 and A/Hong Kong/8/68. Coronavirus infection media was composed of HCoV-NL63 diluted to the appropriate MOI in HBSS. When the mucus wash was completed, viral inoculum was added to the apical side of the tissues. Each experiment included both an untreated control in which ALI was maintained and an untreated control that was submerged in HBTEC-ALI or custom-ALI media for comparison to the viral inoculum-treated groups. The time of incubation varied by viral strain, with HCoV-NL63 incubated on the ALI tissues for 6 h with rocking and A/California/04/09 and A/Hong Kong/8/68 each individually incubated for 1 h with rocking. Following incubation, both the top chamber and the bottom channel were aspirated, the apical surface of the tissue washed three times with 1× HBSS with the final wash collected for reference, and the top chamber was completely aspirated to resume ALI culture. A volume of 60 μL of HBTEC-ALI or custom-ALI media was added to the bottom channel to resume normal culture conditions, with 1 μg/mL TPCK-trypsin maintained in the media of devices that had been inoculated with A/California/04/09 and A/Hong Kong/8/68. At 24 or 48 h intervals p.i., an apical wash using 1× HBSS was performed at 34-37° C. for 1.5 h with rocking to collect both mucus and virus. Specifically, 100 μL of 1× HBSS was added to the apical surface of each tissue and incubated on the tissues for 45 min at 34-37° C. with rocking, subsequently followed by an additional 50 μL wash with 1× HBSS for 45 min at 34-37° C. with rocking and a final 50 μL wash with 1× HBSS for 5 min at room temperature. Apical washings were pooled, collected and stored at −80° C. until processed. Basal media was collected at time points p.i. that correspond to mucus and virus wash collections, and stored at −80 20 C. Following apical wash and basal media collections, 60 μL of HBTEC-ALI or custom-ALI media (including 1 μg/mL TPCK-trypsin for devices that had been inoculated with either A/California/04/09 or A/Hong Kong/8/68) was added to the bottom channel and complete aspiration of the top chamber to resume ALI culture was performed to resume normal culture conditions Supernatant viral RNA was collected from the apical side of ALI tissues and isolated using a QlAamp Viral RNA Mini Kit (Qiagen) following the manufacturer's specifications. Supernatant volumes of 100 μL were brought to 140 μL using HBSS. In order to collect bulk tissue RNA from devices, RLT buffer (Qiagen) with 0.01% v/v 2-mercapto-ethanol (Sigma) was added to both the top and bottom channel to disrupt the differentiated tissue. Tissue RNA was extracted from ALI devices using an RNeasy Micro Kit (Qiagen) per the manufacturer's instructions. One-step quantitative reverse transcription polymerase chain reaction (RT-qPCR) was then performed on extracted RNA samples using a QuantiTect Probe RT-PCR kit (Qiagen) following the standard protocol for a QuantStudio 7 Flex RT-PCR system. Briefly, 7.8 μL of the extracted supernatant viral RNA was used in a 20 μL reaction volume and 3.8 μL tissue RNA was used in a 20 μL reaction volume, and samples were run in duplicate. The reaction was run in an Applied Biosystems QuantStudio 7 Flex System (Thermo Scientific) using the following condition: 50° C. for 20 min, 95° C. for 5 min, 40 cycles of 95° C. for 15 sec and 60° C. for 45 sec. TaqMan primers and probe targeting IAV-M were ordered from Thermo Scientific with the following sequences: FLUAM-7-F: CTTCTAACCGAGGT-CGAAACGTA, FLUAM-161-R: GGTGACAGGAT-TGGTCTTGTCTTTA, FLUAM-49-P6: TCAGGCCCCCT-CAAAGCCGAG, and TaqMan primers and probe targeting HCoV-NL63 (Assay ID: Vi06439673_s1) were ordered from Thermo Scientific. TaqMan Gene Expression Assays (Thermo Scientific) were used to target the following proteins in lung tissue: ACE2 (Hs01085333_m1), TMPRSS2 (Hs01122322_m1), TUBB6 (Hs00603164_m1), and Muc5AC (Hs01365616_m1). Absolute quantification (copies/mL) of supernatant viral RNA was calculated using a standard curve generated from serial dilutions of A/PR/8/34 viral RNA (Charles River Laboratories) or linearized HCoV-NL63 viral RNA (ATCC). Comparative cycle threshold (Ct) values were determined using the method described by Schmittgen and Livak using normalization to the house-keeping gene GAPDH.

Data are presented as mean±standard deviation and were analyzed using graph software. Statistical significance was determined using two-way analysis of variance (ANOVA) with Tukey's or Sidak's post hoc test for multiple comparisons, where appropriate. A p-value lower than 0.05 was considered statistically significant and is indicated in figures as follows: $*P \le 0.05$, $ P \le 0.01$, $*P \le 0.001$, and $****P \le 0.0001$.

The adaptation of the platform for the ALI model allows for inoculation of cultured tissues in each channel apically or basally, sampling of the basal media at regular intervals, and examination of the tissues at the completion of each study, as shown in FIG. 1A. The schematic (left) illustrates the 384 well standard structure upon which each of the individual airway models is situated. At the right, the detailed view shows access to the top chamber (top two wells of the 2×2 array) and the bottom channel (accessed by an inlet and outlet from the bottom two elements of the 2×2 array, respectively.) An exploded-view schematic (FIG. 3A) of this configuration depicts the assembly of the material layers required to establish the microfluidic structure of the ALI platform. Photographs in FIG. 13 depict the ALI platform from an upright view (left), inverted view (right) and over-head view (bottom), with a higher magnification detail of an individual airway model.

Figure 13:
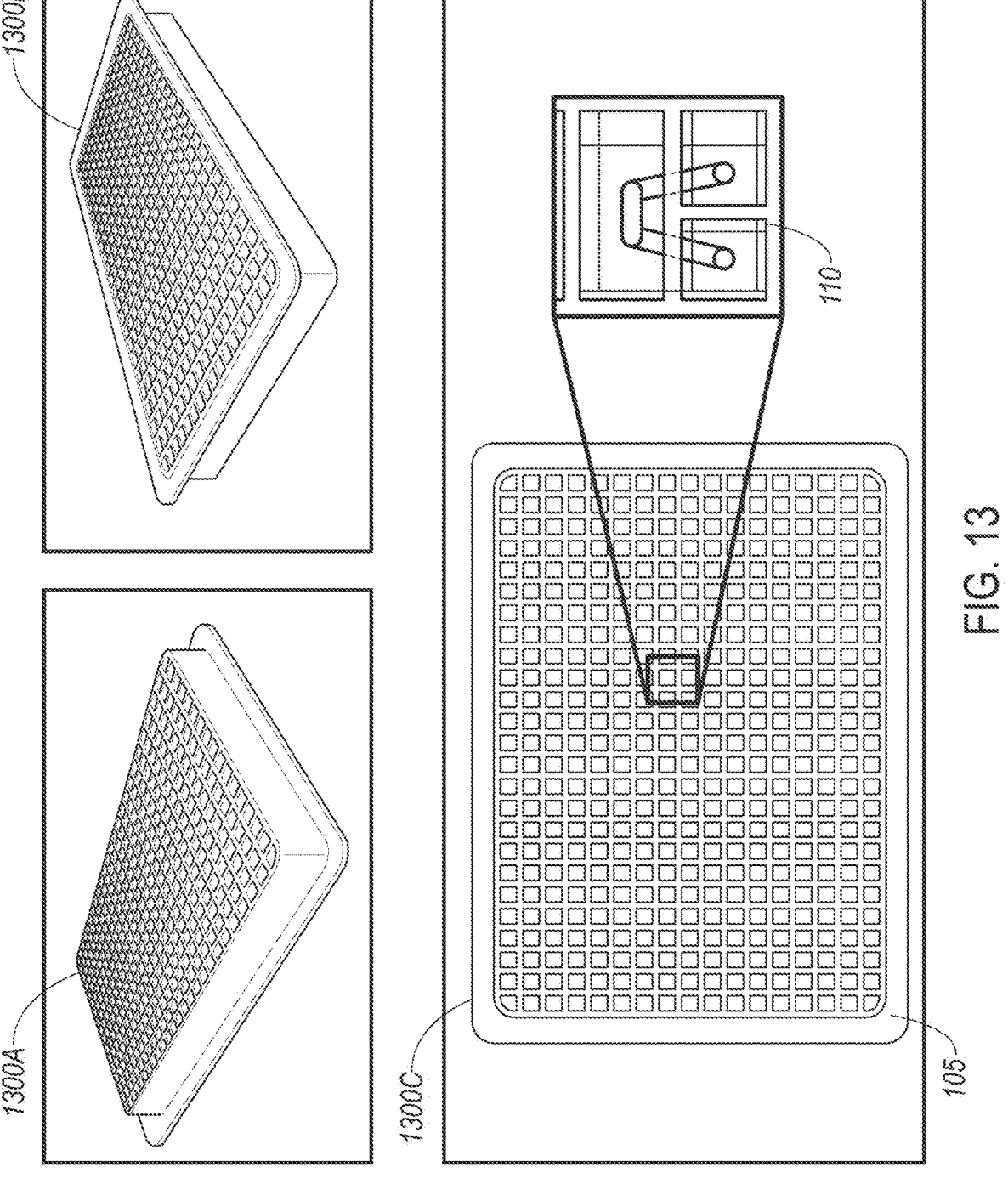
FIG. 13 includes photographs of the upright view (left), inverted view (right) and overhead view (bottom) of the well plate shown in FIGS. 1A and 1B, with magnified view of an individual microfluidic device within the well plate, in accordance with one or more implementations.
Figures 14A, 14B, 14C, 14D:
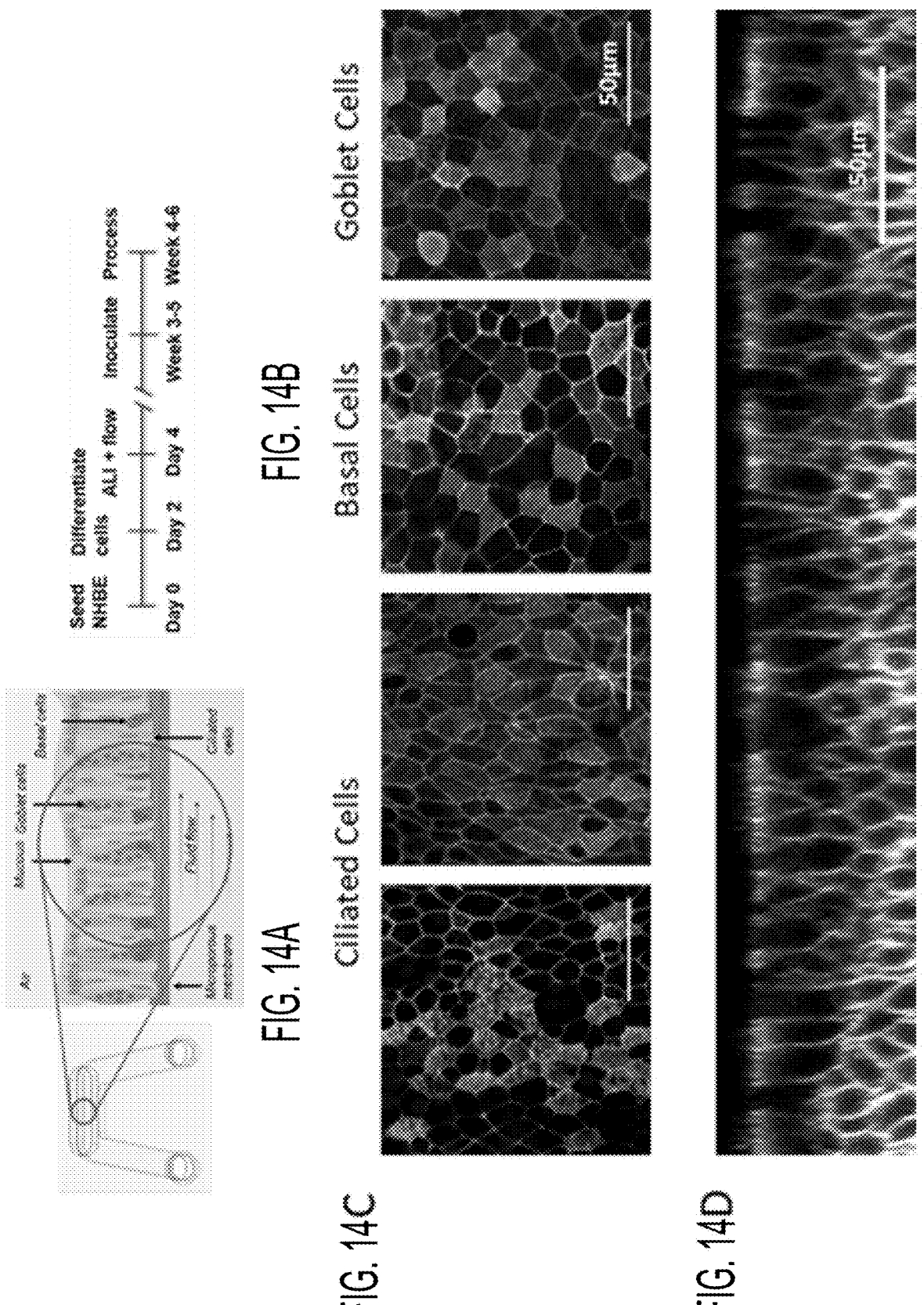
FIG. 14A illustrates a schematic view of the configuration of the biomimetic airway model within the platform described herein.
FIG. 14B illustrates timeline data detailing proliferation, differentiation, inoculation, and processing of tissue in the microfluidic devices described herein.
FIG. 14C illustrates stains of ciliated cells and goblet cells, in accordance with one or more implementations.
FIG. 14D illustrates a high-resolution confocal microscopy 40× z-stack orthogonal image of the pseudostratified epithelium, in accordance with one or more implementations.

FIG. 13 depicts photographs of the upright view (1300A), inverted view (1300B) and overhead view (1300C) of the culture plate 105, with a magnified view of an individual microfluidic device 110 within the well plate 105 platform configuration. First, the ALI system was used to establish the healthy baseline airway model, prepared as described in the Methods section, and morphology and cell populations were evaluated using high resolution confocal microscopy and immunohistochemistry. An illustration depicts the development of a healthy airway model within the well plate 105 (FIG. 14A). The experimental timeline and setup for the system is outlined in FIG. 14B. Fluorescent staining of ciliated cells, goblet cells, and basal cells (FIG. 14C), as well as a cross-section of the pseudostratified epithelial layer (FIG. 14D) are shown for a typical airway tissue within a single device of the ALI model. Our observations for airway tissues in the ALI platform regarding the relative populations of ciliated cells, basal cells, and goblet cells are consistent with our previously reported observations in earlier generations of our airway models as well as with in vivo observations. We also evaluated TransEpithelial Electrical Resistance (TEER) for the airway tissues over time during establishment of the ALI, observing varying kinetics of barrier resistance across different human donor populations but ultimately the same final level of TEER for a given media formulation and protocol (FIG. 14E) We have observed that the behavior of TEER is strongly dependent upon media formulation, which can shift the baseline TEER behavior between different conditions.

FIGS. 14A-14D depict a healthy ALI Airway model. FIG. 14A depicts a schematic illustrating the configuration of the biomimetic airway model within the ALI platform with associated microenvironmental features including differentiated cell populations (ciliated, goblet, basal and club cells) of the mature tissue, apical mucus and periciliary fluid present on mature human airway, and basolateral fluid flow to recirculate nutrients, remove waste products, and oxygenate the media. FIG. 14B shows a timeline detailing proliferation, differentiation, inoculation and processing (sample collection, fixation, imaging, etc.) of the ALI airway tissue over 4-6 weeks. FIG. 14C shows stains of ciliated (acetylated-tubulin, green; β-tubulin, red), basal (CKS, green), and goblet (Muc5ac, green) cells counterstained for nucleic acids (DAPI, blue) and actin (phalloidin, grey) at 40× magnification shown, with a 50 μm scale bar. Donor B is featured as representative. FIG. 14D depicts high-resolution confocal microscopy 40× z-stack orthogonal image of the pseudostratified epithelium with approximately 4 cell layers and 50 μm thick established after culture at 28 d at an ALI. Donor B is featured as representative. FIG. 14E deptics transepithelial Electrical Resistance (TEER) plotted over time for three human primary epithelial cell donor populations, showing that the same ultimate level of barrier function is reached although the kinetics of barrier resistance are different.

We explored the formation of a pseudostratified epithelium at an ALI using freshly harvested human bronchial epithelial cells from research bronchoscopies, labeled DH01, observing robust establishment of airway tissues over periods of 5 weeks or longer in culture in the ALI plates. Panels illustrating the establishment of mature tissue with a pseudostratified morphology, approximately 30-50 μm thick, are provided in FIGS. 15A-D. Here we show 40× images of IF staining of cell populations as described above, including basal cell populations (CK5), goblet cells (Muc5AC), ciliated cells (acetylated tubulin, beta-tubulin), and club cells (scgb1a1, scgb3a2), all with scale bar=100 μm. Also shown is the morphology of mature tissue cultured in the ALI, shown en face at 10× magnification (FIG. 15E), and the presence of mucus droplets formed on the surface of the mature tissue at 40× (FIG. 15F); we also observe robust ciliary beating (see supplementary video) and mucociliary flow.

FIGS. 15A-15F show a healthy ALI airway model with Freshly Harvested Epithelial Cells from Research Bronchoscopies. Panels illustrating establishment of mature tissue with pseudostratified morphology, approximately 30-50 μm thick from freshly harvested airway epithelial cells obtained from living research bronchoscopy donor DH01 are shown in FIGS. 15A-15D. 40× images showing basal cell populations (CKS, green), goblet cells (Muc5AC, green), ciliated cells (acetylated tubulin, green; β-tubulin, red), and club cells (Scgb1a1, red; Scgb3a2, red) counterstained with nucleic acid (DAPI, blue) and actin (phalloidin, grey) with scale bar=100 μm, FIG. 15E shows 10× phase contrast image of mature tissue at 28 d at an ALI with scale bar=100 μm, and FIG. 15F shows 40× phase contrast image of mucus droplets (black arrows) on surface of mature tissue at 28 d at an ALI with scale bar=50 μm. Cells are characterized by robust ciliary beat (see supplementary video) and mucociliary flow.

Figure 16:
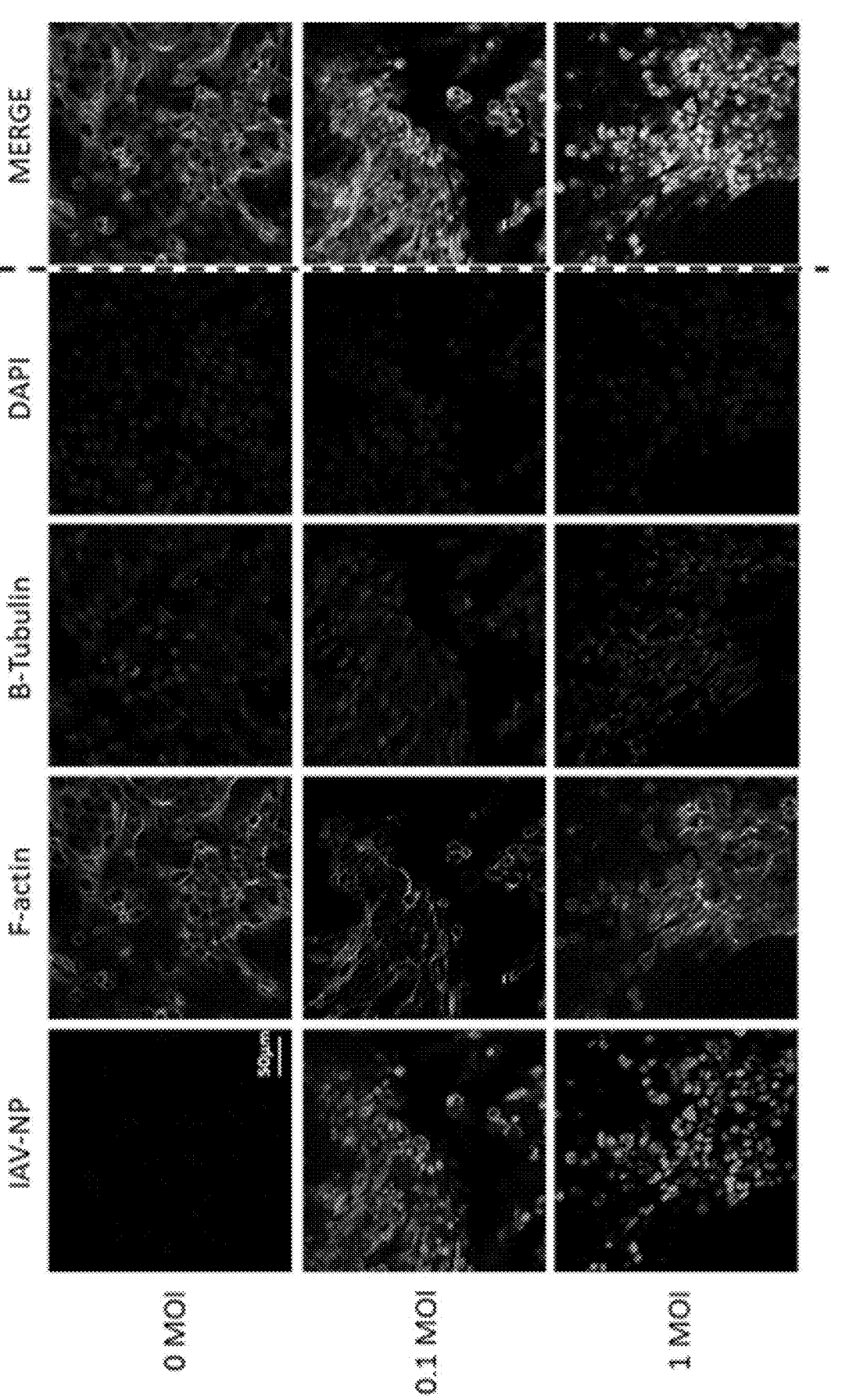
FIG. 16 depicts stain of the nucleoptrotein for IAV, and nucleic acids, in accordance with one or more implementations.

Next, we examined the effect of inoculation of airway ALI cultures with various strains of IAV, including A/California/04/09 H1N1 and A/Hong Kong/8/68 H3N2. In FIG. 16, IF staining of ALI culture devices seeded with living donor DH01 cells and inoculated with various MOIs of A/California/04/09 H1N1 are shown, demonstrating greater abundance of IAV nucleoprotein (NP) as the MOI increases. The 20× images at the apical plane show IAV NP staining across the range of 0.1-10 MOI, with levels increasing substantially as the MOI rises from 0.1 to 1 and again from 1 to 10.

FIG. 16 shows immunofluorescence staining of IAV-infected ALI Airway Tissue. Staining of the nucleoprotein (NP, green) for IAV, actin (phalloidin, grey), β-tubulin (red) and nucleic acids (DAPI, blue), including merged panels for all four stains, within ALI airway tissue developed using freshly harvested epithelial cells from donor DH01 at 48 h p.i., after 5 weeks ALI culture and following inoculation with A/California/04/09 H1N1 (MOI 0, 0.1 or 1). Strong expression of IAV-NP is seen at 48 h p.i. at both MOI 0.1 and 1. Images captured are 40×, z-stacks, slice 24 of 48. Scale bar=50 μm.

Figures 17A, 17B:
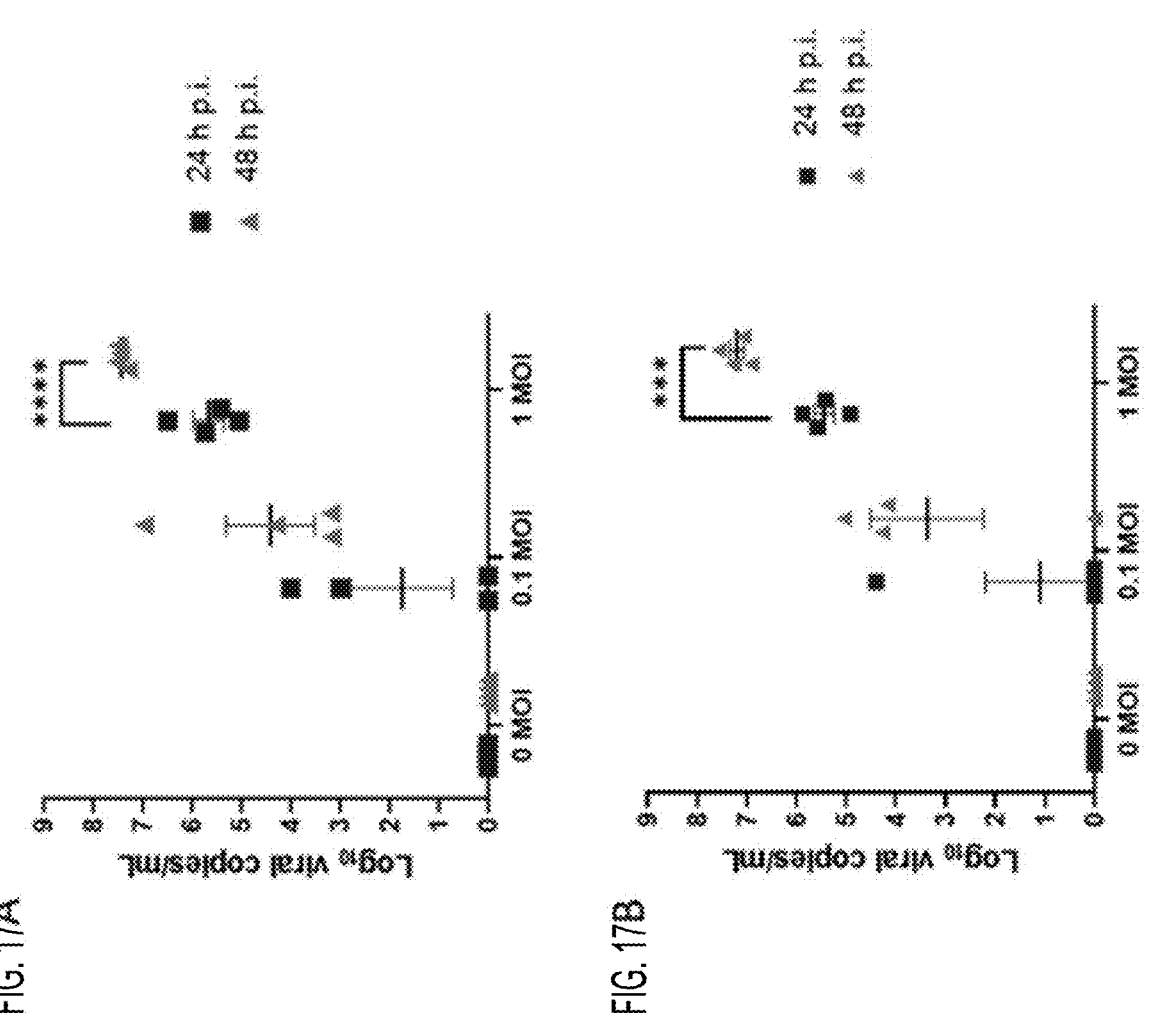
FIGS. 17A and 17B depict RT-qPCR analyses for viral copies in the apical wash of apical tissue.

Measurements of supernatant viral RNA were obtained using RT-qPCR, and are provided in the two panels in FIGS. 17A and 17B. Viral copy numbers after inoculation at MOIs of 0.1 and 1 were measured at 24 and 48 h p.i. for the A/California/04/09 H1N1 strain of IAV (FIG. 17A). In FIG. 17B, companion results for A/Hong Kong/8/68 H3N2 are shown. For the H1N1 and H3N2 strains, viral copies per mL tend to increase with MOI, and continue to rise between 24 and 48 h p.i.

FIGS. 17A and 17B depict RT-qPCR analyses for viral copies in the apical wash of ALI airway tissue at 24 and 48 h p.i. In FIG. 17A illustrated is ALI airway tissue inoculated with A/California/04/09 H1N1 and monitored for an increase in viral load at 24 h intervals with a statistically significant increase in viral copies at 48 h p.i. compared to 24 h p.i. for the MOI 1 condition. In FIG. 17B, ALI airway tissue inoculated with A/Hong Kong/8/68 H3N2 and monitored for an increase in viral load at 24 h intervals with a statistically significant increase in viral copies at 48 h p.i. compared to 24 h p.i. for the MOI 1 condition. Statistical significance: *$p \leq 0.001$ and **$p \leq 0.0001$. N=2 independent experiments with data presented from one representative experiment. Per experiment, N=3-4 tissue replicates per donor, time-point and condition. Replicates that did not meet the minimum signal intensity after 45 PCR cycles are displayed along the x-axis.

To determine if the ALI airway model can be used to evaluate the efficacy of potential antiviral therapeutics, we investigated the effect of the antiviral agent oseltamivir—the most commonly used clinical anti-influenza therapy—for its ability to reduce viral load in IAV-inoculated ALI airway tissue. The active form of oseltamivir, oseltamivir carboxylate, was introduced 2 h before viral inoculation and maintained in the bottom channel of the ALI airway tissues during the course of infection with A/HongKong/8/68 H3N2 virus at various MOIs. Oseltamivir ($>0.1$ μM) significantly reduced influenza replication up to 48 h p.i. (FIGS. 18A and 18B) relative to control tissue devices for the A/Hong Kong/8/68 H3N2 strain at MOI 0.1 and prevented virus-induced disruption to barrier function and epithelial tight junction formation (data not shown). Measurements for viral copies in the ALI airway model reflect those achieved in clinical settings among patients exposed to influenza and treated with oseltamivir, suggesting that the ALI airway model can serve as a preclinical tool to evaluate potential therapies for combating respiratory infections of the human airway.

FIGS. 18A and 18B show infection Kinetics of IAV-inoculated ALI Airway Tissue in Response to Oseltamivir. RT-qPCR analyses for viral copies of the apical wash of ALI airway tissue at 24 and 48 h p.i. in absence (blue) or presence (red=0.01 μM, green=0.1 μM, violet=1 μM, black=10 μM) of oseltamivir (Tamiflu) for two donors labeled Donor B (FIG. 18A) and Donor C (FIG. 18B). ALI airway tissue inoculated with A/Hong Kong/8/68 H3N2 at MOI=0.1, and monitored for viral load over 24 h intervals up to 48 h p.i. with a marked decrease in viral copies in response to oseltamivir dose at both time points. N=2 independent experiments with data presented from one representative experiment. Per experiment, N=3-4 tissue replicates per donor, time-point and condition. Replicates that did not meet the minimum signal intensity after 45 PCR cycles are displayed along the x-axis.

In preparation for testing the viral respiratory infection model with coronaviruses, we probed for transcript expression of cell surface proteins ACE2 and TMPRSS2 known to play central roles in facilitating viral infection by SARS-CoV-2. Both HCoV-NL63 and SARS-CoV-2 gain entry into host cells via the ACE2 receptor, while TMPRSS2 facilitates SARS-CoV-2 infection via cleavage mechanisms, and thus its presence is an important aspect of the model. Data for ACE2 and TMPRSS2 transcripts for cell populations derived from two different donors are plotted on a semi-logarithmic scale in FIG. 19. Data from each donor evaluated show consistent transcript expression for ACE2 and TMPRSS2 between donors. The consistency between these key cellular factors among different donors is encouraging, as it suggests that the platform is capable of supporting proliferation and maturation of tissues derived from numerous donors. Thus, evaluation of many donors can be accommodated in the ALI system both as a healthy model and in the presence of pathogenic challenge.

Figure 19:
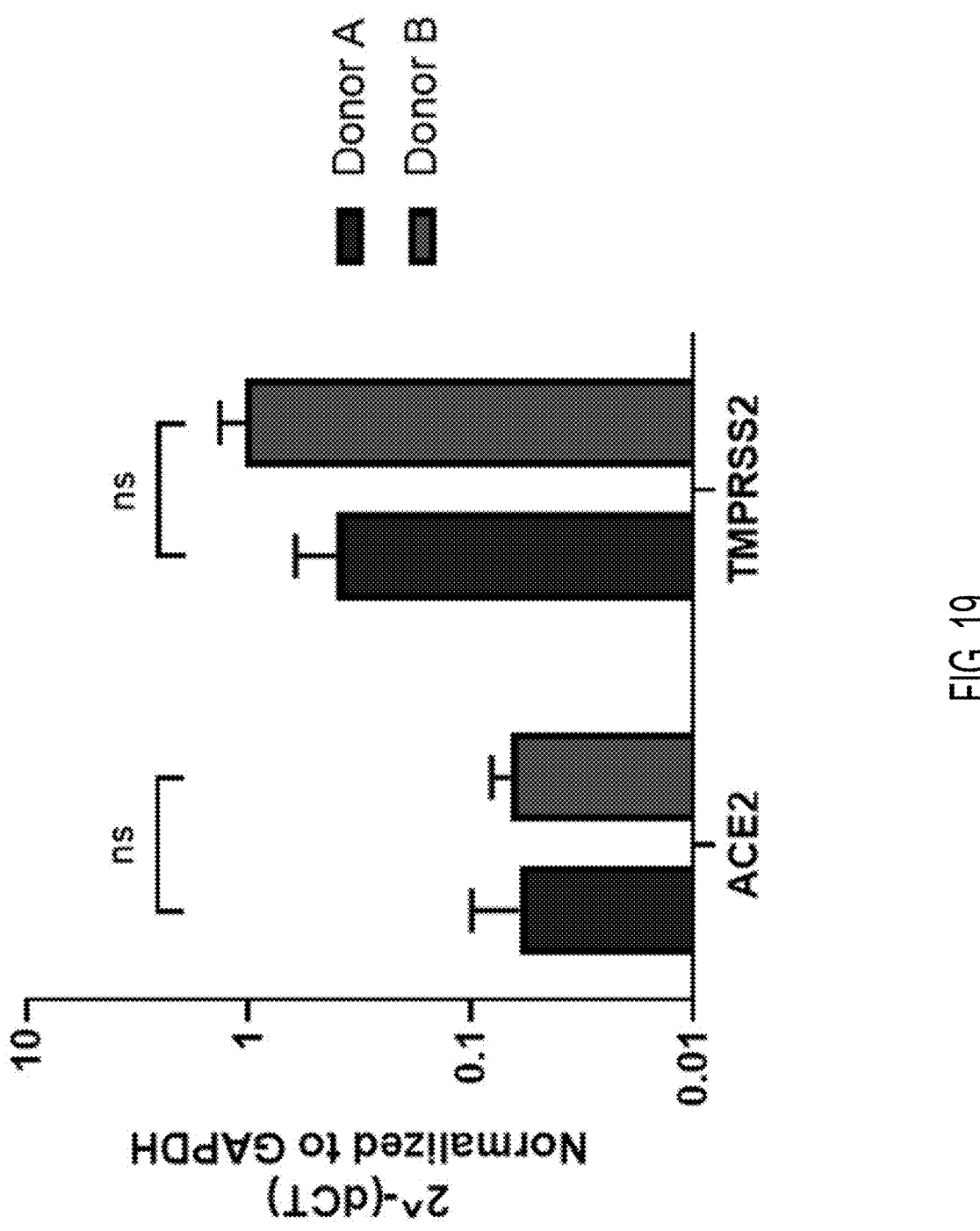
FIG. 19 depicts a comparative quantification of ACE2 and TMPRSS2 in ALI airway tissues, in accordance with one or more implementations.

FIG. 19 shows comparative quantification of ACE2 and TMPRSS2 in ALI Airway Tissues. Transcripts of ACE2 and TMPRSS2, both critical for establishing HCoV-NL63 and SARS-CoV-2 infection, were detected by RT-qPCR from ALI airway tissue. ALI airway tissue from Donor A and B were matured to 4 weeks ALI and shown to have a non-significant (ns) difference in ACE2 and TMPRSS2 gene transcript levels when compared to one another. Comparative CT values were determined using the method described by Schmittgen and Livak and used to determine the relative quantification of gene expression using GAPDH as a reference gene. N=3-4 tissue replicates per donor.

Figures 20A, 20B:
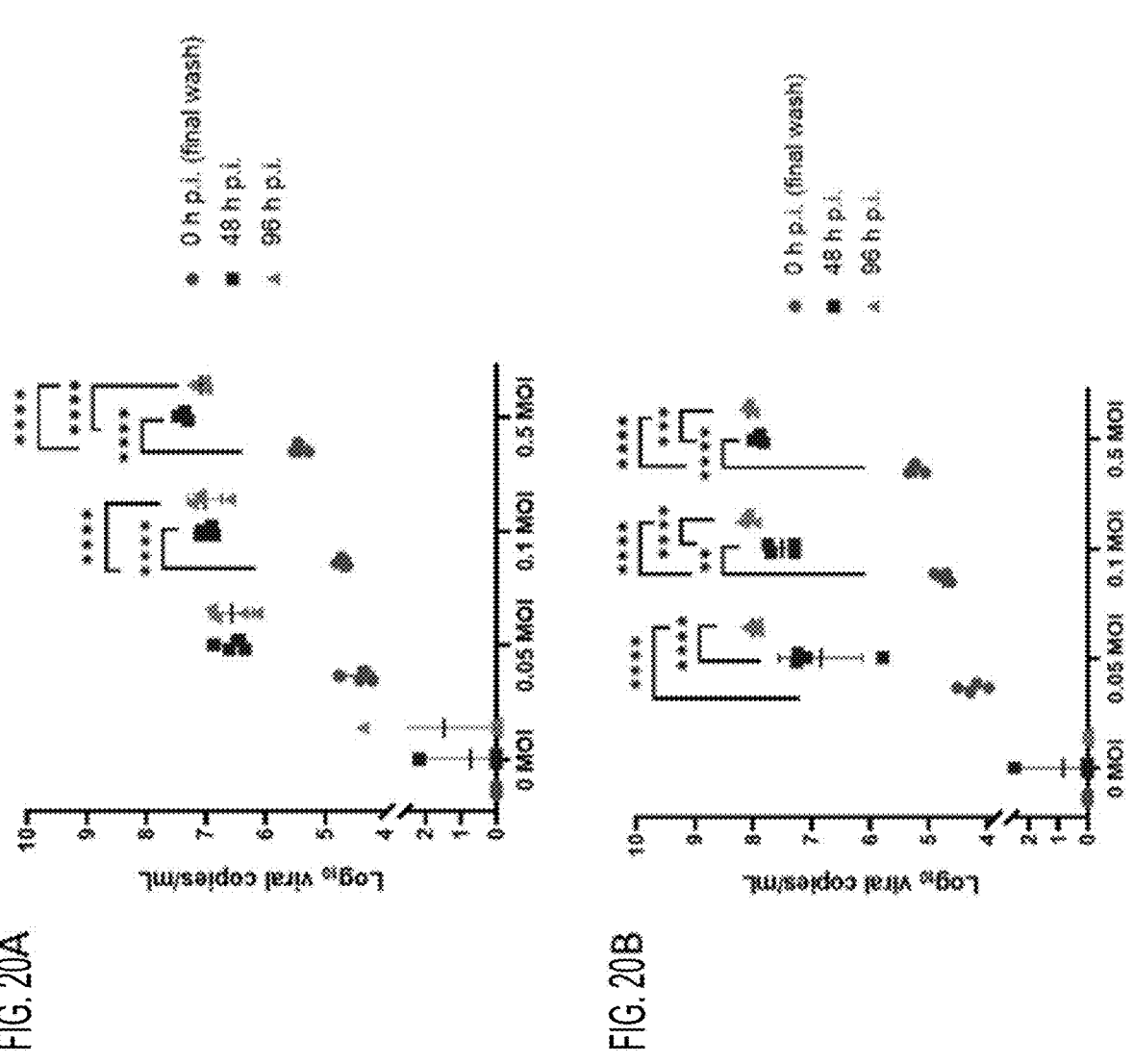
FIG. 20A and FIG. 20B depict infection kinetics of HCoV-NL63-inoculated ALI airway tissue.

We have also investigated viral infection with HCoV-NL63 in the ALI culture system with primary NHBEs, as shown in FIGS. 20A and 20B for two different donor cell populations. In each case, viral copies in the supernatant were measured with RT-qPCR over periods extending to 96 h p.i. and across a range of MOIs. We observed a clear increase in viral load over these time periods for both donors, indicating viral propagation in the airway tissues. Viral copies rose sharply from 0 to 48 h for each MOI tested, while from 48 to 96 h the rate of viral propagation decreased and differed between the two donors.

FIGS. 20A and 20B show Infection Kinetics of HCoV-NL63-inoculated ALI Airway Tissue. RT-qPCR analyses for viral copies in the apical wash of ALI airway tissue at 0, 48 and 96 h p.i. for two human donors showing unique infection kinetic profiles. FIG. 20A shows ALI Donor A airway tissue inoculated with HCoV-NL63 and monitored for an increase in viral load at 48 h intervals with a statistically significant increase in viral copies at 48 and 96 h p.i compared to 0 h p.i. for the MOI 0.1 and 0.5 conditions. Statistical significance: **$p \leq 0.0001$. FIG. 20B shows ALI Donor B airway tissue inoculated with HCoV-NL63 and monitored for an increase in viral load at 48 h intervals with a statistically significant increase in viral copies at 96 h p.i compared to 48 and 0 h p.i. for MOI 0.05, 0.1, and 0.5, as well as a statistically significant increase in viral copies at 48 h p.i. compared to 0 h p.i. for MOI 0.1 and 0.5 conditions. Statistical significance: $p \leq 0.01$, *$p \leq 0.001$, and **$p \leq 0.0001$. N=2 independent experiments with data presented from one representative experiment. Per experiment, N=3-4 tissue replicates per donor, time-point and condition. Replicates that did not meet the minimum signal intensity after 45 PCR cycles are displayed along the x-axis.

The coronavirus HCoV-NL63 enters host cells through the same ACE2 receptor pathway as SARS-CoV-2, and utilizes protein priming via the protease TMPRSS2, and therefore NL63 represents a useful model for studying SARS-CoV-2 infection in a BSL-2 laboratory environment. HCoV-OC43 and SARS-CoV-2 both belong to the betacoronavirus genus, and share common spike protein properties. In FIGS. 21A, 21B, 21C, and 21D, we show infection kinetics determined by RT-qPCR for each of HCoV-NL63 (FIGS. 9A and 9C) and HCoV-OC43 (FIGS. 9B and 9D) across 12 d p.i. and across a range of MOIs, and we observe a strong increase in viral load versus MOI with distinct rates of infection for each strain.

FIGS. 21A-21D show infection of coronavirus strains in ALI model. RT-qPCR analyses for viral copies of HCoV-NL63 (FIGS. 21A and 21C) and HCoV-OC43 (FIGS. 21B and 21D) in the apical wash of ALI airway tissue model from a single donor, measured over 12 days across three different MOIs (0, 0.05, 0.5). FIG. 21A shows ALI airway tissue inoculated with HCoV-NL63 and monitored for an increase in viral load at 48 h intervals with a statistically significant increase in viral copies at 48 and 96 h p.i. compared to 0 h p.i. for the MOI 0.05 condition, as well as a statistically significant increase at 48 h p.i. compared to 0 h p.i. for the MOI 0.5 condition. FIG. 21B shows ALI airway tissue inoculated with HCoV-OC43 and monitored for an increase in viral load at 48 h intervals with a statistically significant increase in viral copies at 48 and 96 h p.i. compared to 0 h p.i. for the MOI 0.5 condition. Statistical significance: *$p \leq 0.05$ and **$p \leq 0.01$. N=4-5 tissue replicates per donor, time-point and condition. Replicates that did not meet the minimum signal intensity after 45 PCR cycles are displayed along the x-axis. Viral copy number versus day post-infection shown for HCoV-NL63 in FIG. 21C, and HCoV-OC43 in FIG. 21D is shown for each MOI as indicated in the legends.

Camostat mesylate (CM) is a serine protease inhibitor reported to partially block infection by HCoV-NL63 in Calu-3 cells and IAV in human primary bronchial epithelial cells and is under investigation as a treatment for SARS-CoV-2 in an ongoing clinical trial. Here we evaluate the effect of CM administered to ALI airway tissues cultured with human primary epithelial airway cells and inoculated with HCoV-NL63 across a range of MOIs. In FIG. 22, we show infection kinetics for the HCoV-NL63 strain across a range of MOIs for untreated versus 20 μM CM-treated cultures in ALI . While the scatter limits statistical significance, qualitatively we observe that CM treatment of airway tissues infected with HCoV-NL63 reduces viral copy number at both the 48 and 96 hour time points, particularly for the MOI=0.005 condition.

FIG. 22 shows the example efficacy of camostat mesylate against hCOV-NL63-inoculated ALI Airway Tissue. RT-qPCR analyses for viral copies in the apical wash of ALI airway tissue at 0, 48 and 96 h p.i. with HCoV-NL63 across multiple MOIs. Solid lines show viral copies for MOI 0 (red), MOI 0.005 (blue) and MOI 0.05 (green) when treated with vehicle (DMSO), and dashed lines show corresponding viral copies when treated with 20 μM camostat mesylate. N=2-4 tissue replicates per donor, time-point and condition. Replicates that did not meet the minimum signal intensity after 45 PCR cycles are displayed along the x-axis.

In the example experimental data described herein above (which is NOT intended to be limiting in any respect), we leverage the ALI platform to create a high-throughput airway infection model to assist in the development of therapeutics to treat respiratory viral infections. To do so, a barrier tissue model was developed at an ALI with human primary tracheobronchial cells, establishing a pseudostratified epithelium, and cultured atop a semipermeable membrane with independent flow control for each device in the basal channel. The data presented demonstrate a robust example model for the human airway using primary tracheobronchial epithelial cells, with a physiologically representative distribution of cell populations of ciliated, basal, and goblet cells and a pseudostratified epithelial layer morphology. Human primary epithelial airway cultures established using commercial sources of cadaver tissues were evaluated, as well as fresh bronchial epithelial cells obtained from healthy control subjects via research bronchoscopy.

The latter approach represents a potential pathway toward in vitro investigation of respiratory infections as a function of gender, age and co-morbidities.

This airway model was applied to the investigation of respiratory viral infections including IAV, HCoV-OC43 and HCoV-NL63, and infection kinetics were evaluated across multiple viral strains, donor populations, MOIs, and time points. Experiments conducted with multiple donor populations of NHBE cells suggest the potential of this system for conducting studies of donor-dependent mechanisms of infection and responses to therapeutic interventions. Key advantages of this platform over existing in vitro platforms include the use of human primary tracheobronchial epithelial cells cultured at an ALI, a more physiologically relevant cell-to-media ratio with smaller, more convenient cell culture area than current standard Transwell® cultures, integrated pumping of basal media to maintain precision control over solute concentration and to avoid the development of non-physiological gradients, and compatibility with high resolution and real-time imaging. While certain existing organ-on-chip models possess some of these advantages, they are typically low-throughput systems designed for research environments, and are often incompatible with workflows and standard instrumentation in pharmaceutical laboratories. Considering the throughput limitations of the competing organ-on-chip models, the ALI platform offers an unmatched capacity that enables large combinations of conditions, such as evaluation of three therapeutics across four MOIs and time points with two viral strains and four replicates for each condition simultaneously on a single plate. The ALI platform combines the high throughput, precision control and physiological relevance necessary to serve as a powerful tool for applications in disease modeling, drug development, and screening.

An important need in the field of respiratory virus research is the establishment of robust in vitro disease models that provide the precision, validation, throughput, and utility necessary for routine operation in drug development laboratories. Here, we deployed the airway tissue model successfully in the ALI platform to investigate infections of two pandemic strains of IAV; A/California/04/09 H1N1 and A/HongKong8/68 H3N2. Infections were monitored using a combination of IF and RT-qPCR, across a range of MOIs and time points, providing a strong foundation for evaluation of therapeutic interventions. As a proof of concept, oseltamivir dosing of the ALI airway model was shown to reduce viral copies of A/HongKong8/68 H3N2 across two donors, demonstrating the potential of this system for screening therapeutic compounds for respiratory viruses. Finally, infection kinetics were established human primary bronchial epithelial cells with two different human coronaviruses (HCoV-NL63 and HCoV-OC43), and treatment with the serine protease inhibitor camostat mesylate resulted in an observed reduction in viral copies, consistent with activity of CM against the TMPRSS2-mediated viral entry.

The example human airway tissue model has applicability to respiratory viruses including coronaviruses, and we have demonstrated the relevance of this model to monitoring pathogen infection kinetics. To investigate the applicability of our model to novel viral pathogens, we examined the ability of HCoV-NL63, an alpha coronavirus sharing the same host entry receptor as SARS-CoV-2, to infect and replicate within ALI. We confirmed the presence of ACE2 and TMPRSS2 transcripts in the primary human cells within our model and successfully infected the ALI airway model with HCoV-NL63 across a range of MOIs and for two different donor human primary epithelial cell populations. We directly compared infection with HCoV-NL63 and HCoV-OC43 in ALI experiments, exploring differences in infection kinetics between these two strains of coronavirus. This example platform model for infection with HCoV-NL63 represents an important example capability for studying coronavirus infections and potentially evaluating therapeutics, building on approaches that use cell lines in high-throughput systems or human primary lung cells in standard Transwell® formats. Finally, we have demonstrated for the first time efficacy of a known antiviral agent in a high-throughput human primary cell-based airway platform, clearly showing the effect of the compound in a dose-responsive manner and with statistical significance in a single 96-device experiment. In light of current challenges in identifying and developing therapeutic agents in response to emerging respiratory viral diseases, the ability rapidly assess efficacy in a human relevant platform and to evaluate donor-to-donor variability efficiently, a higher throughput system such as presented here is critical.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements, and features discussed in connection with one implementation are not intended to be excluded from a similar role in other implementations.

The phraseology and terminology used herein is for the purpose of description and should not be regarded as limiting. The use of "including," "comprising," "having," "containing," "involving," "characterized by," "characterized in that," and variations thereof herein is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the terms "about" and "substantially" will be understood by persons of ordinary skill in the art and will vary to some extent depending upon the context in which they are used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations.

References to any act or element being based on any information, act, or element may include implementations where the act or element is based at least in part on any information, act, or element.

Any implementation disclosed herein may be combined with any other implementation or embodiment, and references to "an implementation," "some implementations," "one implementation," or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description, or any claim are followed by reference signs, the reference signs have been included to increase the intelligibility of the drawings, detailed description, and claims. Accordingly, neither the reference signs nor their absence has any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A microfluidic cell culturing device, comprising:
a first channel having a first inlet port and a second inlet port, sidewalls of the first channel defined in a first layer, a bottom surface of the first channel defined by an optically clear layer coupled to the first layer, each of the first inlet port and the second inlet port defined at least in part in a second layer;
a membrane layer having a first surface coupled to the first layer defining sidewalls of the first channel and a second surface coupled to the second layer, the membrane layer comprising a semipermeable membrane that forms a top surface of the first channel, the membrane layer comprising a first opening aligned with the first inlet port and a second opening aligned with the second inlet port; and
a chamber defined as a slot in the second layer coupled to the second surface of the membrane layer, the chamber having a length greater than at least twice a width of the chamber, the chamber comprising a first divot defined in the second layer at a first end of the chamber and a second divot defined in the second layer at a second end of the chamber, the chamber exposing a portion of the second surface of the membrane layer to an external environment via an opening in the second layer, wherein the chamber overlaps a portion of the first channel across the membrane layer.

2. The microfluidic cell culturing device of claim 1, wherein the chamber further comprises one or more conductive traces configured to attach to an electrical measurement device.

3. The microfluidic cell culturing device of claim 1, wherein at least one of the first inlet port, the second inlet port, or the chamber, is in fluid communication with a respective reservoir of a culture plate.

4. The microfluidic cell culturing device of claim 1, wherein the chamber is configured to receive suspension cells or adherent cells, and the exposed portion of the second surface of the membrane layer is configured to culture one or more cells.

5. The microfluidic cell culturing device of claim 1, wherein the first layer is coupled to the membrane layer using thermal compression.

6. The microfluidic cell culturing device of claim 1, wherein the chamber further comprises a step feature configured to retain cell suspension during seeding of the microfluidic cell culturing device.

7. The microfluidic cell culturing device of claim 6, wherein the step feature has a height in a range of 250 microns to 2.5 millimeters.

8. The microfluidic cell culturing device of claim 6, wherein the step feature further comprises a draft angle configured to reduce bulging of a cell suspension droplet positioned in the chamber.

9. The microfluidic cell culturing device of claim 1, wherein the chamber comprises a rectangular footprint or a slotted footprint.

10. The microfluidic cell culturing device of claim 1, wherein the semipermeable membrane comprises pores having a pore size in a range of 0.4 to 8 microns.

11. The microfluidic cell culturing device of claim 1, wherein the first layer or the second layer comprise one or more of cyclo-olefin polymers, polyetherimide, polystyrene, polycarbonate, or polymethylmethacrylate.

12. A culture plate, comprising:
a plurality of well reservoirs; and
a plurality of microfluidic devices, each of the plurality of microfluidic devices comprising:
a first channel having a first inlet port and a second inlet port, sidewalls of the first channel defined in a first layer, a bottom surface of the first channel defined by an optically clear layer coupled to the first layer, each of the first inlet port and the second inlet port defined at least in part in a second layer;
a membrane layer having a first surface coupled to the first layer defining the first channel and a second surface coupled to the second layer, the membrane layer comprising a semipermeable membrane that forms a top surface of the first channel, the membrane layer comprising a first opening aligned with the first inlet port and a second opening aligned with the second inlet port; and
a chamber defined as a slot in the second layer coupled to the second surface of the membrane layer, the chamber having a length greater than at least twice a width of the chamber, the chamber comprising a first divot defined in the second layer at a first end of the chamber and a second divot defined in the second layer at a second end of the chamber, the chamber exposing a portion of the second surface of the membrane layer to an external environment via an opening in the second layer, wherein the chamber overlaps a portion of the first channel across the membrane layer.

13. The culture plate of claim 12, the chamber of each of the plurality of microfluidic devices further comprises one or more conductive traces configured to attach to an electrical measurement device.

14. The culture plate of claim 12, wherein at least one of the first inlet port, the second inlet port, or the chamber, of each of the plurality of microfluidic devices, is coupled to a respective well reservoir of the plurality of well reservoirs.

15. The culture plate of claim 12, wherein the chamber of each of the plurality of microfluidic devices is configured to receive suspension cells or adherent cells, and the exposed portion of the second surface of the membrane layer of each of the plurality of microfluidic devices is configured to culture one or more cells.

16. The culture plate of claim 12, wherein the chamber of each of the plurality of microfluidic devices further comprises a step feature configured to retain cell suspension during seeding of the plurality of microfluidic devices.

17. The culture plate of claim 16, wherein the step feature has a height in a range of 250 microns to 2.5 millimeters.

18. The culture plate of claim 16, wherein the step feature further comprises a draft angle configured to reduce bulging of a cell suspension droplet positioned in the chamber.

19. The culture plate of claim 16, wherein the first layer or the second layer of each of the plurality of microfluidic devices comprises one or more of cyclo-olefin polymers, polyetherimide, polystyrene, polycarbonate, or polymethyl-methacrylate.

20. The culture plate of claim 16, further comprising one or more pumps each in fluid communication with a respective first inlet port or a respective second inlet port of a respective microfluidic device of the plurality of microfluidic devices.

* * * * *